US008420634B2

(12) United States Patent
Anzini et al.

(10) Patent No.: US 8,420,634 B2
(45) Date of Patent: Apr. 16, 2013

(54) AMIDINE, THIOUREA AND GUANIDINE DERIVATIVES OF 2-AMINOBENZOTHIAZOLES AND AMINOBENZOTHIAZINES FOR THEIR USE AS PHARMACOLOGICAL AGENTS FOR THE TREATMENT OF NEURODEGENERATIVE PATHOLOGIES

(75) Inventors: Maurizio Anzini, Seina (IT); Antonio Giordani, Pavia (IT); Francesco Makovec, Milan (IT); Andrea Cappelli, Grosseto (IT); Salvatore Vomero, Siena (IT); Gianfranco Caselli, Milan (IT); Lucio Claudio Rovati, Monza (IT)

(73) Assignee: Rottapharm S.p.A., Milan (IT)

( * ) Notice: Subject to any disclaimer, the term of this patent is extended or adjusted under 35 U.S.C. 154(b) by 233 days.

(21) Appl. No.: 12/679,620

(22) PCT Filed: Sep. 22, 2008

(86) PCT No.: PCT/EP2008/062636
§ 371 (c)(1),
(2), (4) Date: Mar. 23, 2010

(87) PCT Pub. No.: WO2009/040331
PCT Pub. Date: Apr. 2, 2009

(65) Prior Publication Data
US 2010/0197670 A1 Aug. 5, 2010

(30) Foreign Application Priority Data
Sep. 24, 2007 (IT) .................................. TO07A0665

(51) Int. Cl.
*A61K 31/5415* (2006.01)
(52) U.S. Cl.
USPC ........................................ 514/224.2; 544/50
(58) Field of Classification Search ...................... 544/50
See application file for complete search history.

(56) References Cited

FOREIGN PATENT DOCUMENTS
EP 1 669 072 A1 6/2006
JP 64003172 A 1/1989

OTHER PUBLICATIONS

V. Ambrogi, et al., "Studies on annelated 1,4-benzothiazines and 1,5-benzothiazepines. IV. Synthesis and biological activity of new 1-substituted derivatives of 4H-s-triazolo[3,4-c]-1,4-benzothiazine and 4,5-dihydro-s-triazolo[3,4-d]-1,5-benzothiazepine," Eur J. Med. Chem., 1991, pp. 835-838, No. 26.
V. Ambrogi, et al., Synthesis, antibacterial and antifungal activities of several new benzo-naphtho-and quinolino-1,4-thiazine and 1,5-thiazepine derivatives*, Eur J. Med. Chem., 1990, pp. 403-411, No. 25.

Manisha V. Deshmukh; New Synthesis of Some 2-Methyl (1,2,4) Triazolo (5,1-b) Benzothiazoles; Indian Journal of Heterocyclic Chemistry, vol. 10, pp. 315-316, Apr.-Jun. 2001.
Alfonzo D. Jordan et al.; Efficient Conversion of Subtituted Aryl Thioureas to 2-Aminobenzothiazoles Using Benzyltrimethylammonium Tribromide; J. Org. Chem., vol. 68, No. 22, pp. 8693-8696, 2003.
Srinivasachari Rajappa et al.; Quinone-Imides: Regiospecificity of Nucleophilic Attack on N-Alkanesulphonyl-N'-Alkanoyl 1,4-Benzoquinone-Imines; Tetrahedron, vol. 42, No. 20, pp. 5739-5746, 1986.
Alfred Courtin; 177. Notiz zur Synthesis von Alkyl-, Cycloakyl-und Aryl-3-aminophenylsulfonen; Helvetica Chimica Acta, vol. 64, Fasc. 6, pp. 1849-1853, 1981.
Akira Miyashita et al.; Electrophilic Cyanations. I. Synthesis of Thiocyanato-Heteroarenes and Tosylheteroarenes from Mercapto-Heteroarenes Using p-Toluenesulfonyl Cyanide; Heterocycles, vol. 45, No. 4, pp. 745-755, 1997.
Joseph Smith et al.; Solid and Solution Phase Organic Syntheses of Oligomeric Thioureas; J. Org. Chem., vol. 61, No. 25, pp. 8811-8818, 1996.
Prof. Dr. H. A. Staab; Syntheses Using Heterocyclic Amides (Azolides); New Methods of Preparative Organic Chemistry IV; vol. 1, No. 7, pp. 351, 353-367, 1962.
Stephen Turner et al.; Antihypertensive Thiadiazoles. 2. Vasodilator Activity of Some 2-Aryl-5-guanidino-1,3,4-thiadizoles; Journal of Medicinal Chemistry, vol. 31, No. 5, pp. 906-913, 1988.
Melissa L. P. Price et al.; Design of Novel N-(2,4-Dioxo-1,2,3,4-tetrahydro-thieno[3,2-d]pyrimidin-7-yl)-guanidines as Thymidine Phosphorylase Inhibitors, and Flexible Docking to a Homology Model; Bioorganic & Medicinal Chemistry Letters; vol. 13, pp. 107-110, 2003.
Royal J. Gay et al.; Optimum Reaction Conditions for Human Lactate Dehydrogenase Isoenzymes as They Affect Total Lactate Dehydrogenase Activity; Clinical Chemistry Laboratory, vol. 14, No. 8, pp. 740-753, 1968.
Alan M. Palmer et al.; The Role of Sodium Channels in Disease; Drug News Perspect; vol. 14, No. 9, pp. 568-576; Nov. 2001.

(Continued)

*Primary Examiner* — Brian McDowell
(74) *Attorney, Agent, or Firm* — Sughrue Mion, PLLC

(57) ABSTRACT

Amidine, thiourea and guanidine derivatives of appropriately substituted 2-aminobenzothiazoles, 2-amino-3,1-4H-benzothiazines and 3-amino-1,4-3H-benzothiazines, as understood from formula (I), the related pharmaceutically acceptable salts and solvates thereof:

Formula (I):

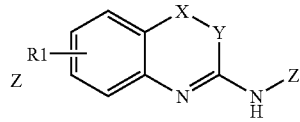

and the use of the products and the corresponding pharmaceutical formulations for the treatment of neurodegenerative pathologies such as cerebral ischemia, neurodegeneration induced by cranial trauma, Alzheimer's disease, Multiple Sclerosis and Amyotrophic Lateral Sclerosis.

5 Claims, No Drawings

OTHER PUBLICATIONS

R.M. Lopachin et al.; Effects of Ion Channel Blockade on the Distribution of Na, K, Ca and Other Elements in Oxygen-Glucose Deprived CA1 Hippocampal Neurons; Neuroscience vol. 103, No. 4, pp. 971-983, 2001.

Philippe Raymond Loiseau et al.; Synthesis and Anthelminthic Evaluation of 2-Amidino-1,3,4-Oxa and 1,3,4-Thiadiazoles, Structurally Related to Tetramisole; IL Farmaco, vol. 45, No. 9, pp. 953-963, 1990.

Kevin Pan et al.; The Synthesis of Aminobenzothiazoles from 2,3-Biaryl-5 anilino- $\Delta^3$-1,2,4-thiadiazolines; Synthetic Communications, vol. 33, No. 12, pp. 2053-2060, 2003.

S.E. Abbas et al.; Synthesis and Antimicrobial Activity of Some New Thiazolidinone Derivatives; Egypt J. Pharm. Sci., vol. 34, No. 1-3, pp. 195-205, 1993.

G.C. Singh; Synthesis of N-Ethyl-N-2-Benzothiazolyl Guanidines and their use as Possible Algaecides; Journal Indian Chem. Soc., vol. 45, No. 1, 1968.

D.R. Shridhar et al.; Synthesis of Some New N-Benzothiazinyl-N'-aryl/pyridyl-thioureas as Potential Anthelmintic Agents; Indian Journal of Chemistry; vol. 20B, pp. 471-473, Jun. 1981.

S. Jayakumar et al.; Synthesis of novel heterocyclic fused 1,3-diazabuta-1,3-dienes and accompanying rearrangements in their cycloaddition reactions with ketenes: synthesis of heterocyclic fused pyrimidinone derivatives; Tetrahedron, vol. 60, pp. 4315-4324, Feb. 12, 2004.

Mirko Buchholz et al.; The First Potent Inhibitors for Human Glutaminyl Cyclase: Synthesis and Structure-Activity Relationship; J. Med. Chem., vol. 49, pp. 664-677, 2006.

H. Charcosset et al.; Etude de la décomposition thermique de l'oxalate de nickel; Bulletin De La Société Chimique De France, 1968.

Yong-Qian Wu et al.; Formation of Nitrogen-containing Heterocycles Using Di(imidazole-l-yl) methanimine; J. Heterocyclic Chem., vol. 40, pp. 191-193; Jan.-Feb. 2003.

V. L. de M. Guarda et al.; Synthesis and microbiological activity of some 2H-1,4-Benzothiazin-3-one derivatives; vol. 6, No. 1, pp. 49-54, 2000.

Kalpana Bhandari et al.; Synthesis of tetrahydronaphthyl thioureas as potent appetite suppressants; Bioorganic & Medicinal Chemistry; vol. 12, pp. 4189-4196, 2004.

Alan R. Katritzky et al.; 1-(Alkyl/Arylthiocarbamoyl) benzotriazoles as Stable Isothiocyanate Equivalents: Synthesis of Di-and Trisubstituted Thioureas; J. Org. Chem.; vol. 69, pp. 2976-2982, 2004.

Elizabeth A. Jefferson et al.; Biaryl guanidine inhibitors of in vitro HCV-IRES activity; Bioorganic & Medicinal Chemistry Letters; vol. 14, pp. 5139-5143, 2004.

Helge Eilers, MD et al.; Different Effects of Volatile Anesthetics and Polyhalogenated Alkanes on Depolarization-Evoked Glutamate Release in Rat Cortical Brain Slices; Anesth Analg, vol. 88, pp. 1168-1174, 1999.

Dieter R. Riddall et al.; A Novel Drug Binding Site on Voltage-Gated Sodium Channels in Rat Brain; Molecular Pharmacology; vol. 69, No. 1, pp. 278-287, 2006.

Vinay S. Misra et al.; Possible Antituberculous Compounds. Part XI. $N_{-2-}$ Benzothiazolyl- and $N_{-3-}$ Quinolyl-amidines; Journal Indian Chem. Soc., vol. 39, No. 3, pp. 209-210, 1962.

Huey-Min Wang et al.; Synthesis of 2-Aryl [1,2,4] Triazolo [5, 1-6] Benzothiazoles, OPPI Briefs, vol. 28, No. 3, 1996.

F. Russo; Derivati Della Tiourea Piridil-E Benzotiazolil-Sostituiti; Boll. Chim. Farm., pp. 252-256, 1961.

Fabiola Téllez et al.; Dithiocarbamates, Thiocarbamic Esters, Dithiocarboimidates, Guanidines, Thioureas, Isothioureas, and Tetraazathiapentalene Derived from 2-Aminobenzothiazole; Eur. J. Org. Chem.; pp. 4203-4214, 2004.

P.N. Bhargava et al.; Synthesis and Spectral Behaviour of Some New (Substituted) Benzothiazolyl Guanidines; Current Science, vol. 43, No. 2, pp. 33-36, Jan. 20, 1974.

P.N. Bhargava et al.; Synthesis of Some New N-o-Tolyl-N'-2-(substituted) Benzothiazolylguanidines; New Compounds, vol. 12, pp. 558-559, May 1969.

AMIDINE, THIOUREA AND GUANIDINE DERIVATIVES OF 2-AMINOBENZOTHIAZOLES AND AMINOBENZOTHIAZINES FOR THEIR USE AS PHARMACOLOGICAL AGENTS FOR THE TREATMENT OF NEURODEGENERATIVE PATHOLOGIES

The present invention relates to novel amidine, thiourea and guanidine derivatives of 2-aminobenzothiazole, 2-amino-3, 1-4H-benzothiazine and 3-amino-1,4-3H-benzothiazine, the relevant pharmaceutically acceptable salts and solvates thereof and the use of said products and corresponding pharmaceutical formulations for the treatment of neurodegenerative pathologies.

INTRODUCTION

Even though studies using animal models conducted during the 1990s demonstrated that, for a wide range of products, blocking ionotropic glutamatergic receptors could lead to pharmacologically significant effects in the treatment of neurodegenerative pathologies, ranging from cerebral ischemia, neurodegeneration induced by cranial trauma (traumatic brain injury—TBI), to the treatment of Alzheimer's Disease (AD), and even the treatment of Multiple Sclerosis (SM) and Amyotrophic Lateral Sclerosis (ALS), subsequent clinical testing, especially conducted in the field of ischemia, TBI and dementia did not yield positive results, except for memantin in the case of dementia. Despite this, many structurally diverse products and with diverse purposes (NMDA, NMDA/Gly-site, AMPA) have been tested clinically (Curr. Opin. Pharmacol. 2006, 6, 1, 53-60; Neurobiol Dis., 2003, 12(1), 82-8). In phase III studies, NMDA glutamate site antagonists, such as Selfotel and Midafotel, have not demonstrated any efficacy in the treatment of ischemia; the same also applies to the allosteric NMDA receptor modulators Ifenprodil and Eliprodil, and the latter has also been shown to be ineffective in the treatment of multiple sclerosis. The NMDA antagonist Remacemide has been suspended after being shown to be ineffective in the treatment of epilepsy, Parkinson's disease and Huntington's disease. The NMDA receptor glycine site antagonist that has reached the most advanced stage of clinical research (phase III for the treatment of cerebral ischemia), Gavestinel, has been withdrawn due to lack of efficacy. Even though there is no doubt that the glutamatergic system, and its hyperactivation in particular, has a significant role in the neurodegenerative phenomena underlying the aforementioned pathologies, the lack of clinical success obtained by this approach has been attributed to numerous causes, such as excessive toxicity due to the NMDA receptor competitive antagonists, the poor penetration of the glycine site antagonists into the central nervous system, and the lack of suitable strength in other cases.

One obvious result is that despite the considerable efforts of the scientific community, pharmacological agents capable of effectively counteracting neurodegenerative pathologies such as those induced by cerebral ischemia or cranial trauma (TBI), Alzheimer's disease, multiple sclerosis and amyotrophic lateral sclerosis are still lacking, maintaining interest into research in this field, and particularly the exploration of alternative strategies to direct action on the glutamatergic system, at a high level.

Neuronal voltage-dependent sodium channels are present in a wide variety of isoforms, mostly resulting from the combination of an alpha subunit with at least 3 different beta subunits. In turn, the alpha subunits exist as numerous splicing variants, thus giving rise to several potential oligomers; consequently, it is very complex not only to produce inhibitors selective for an individual type of channel, but also to characterise the activity profile of an inhibitor on different channels. In the past, sodium channel conduction inhibitors had been used in the treatment of epilepsy, and more recently it has been highlighted how, when appropriately processed, such agents can be potential drugs, effective for the treatment of neurodegenerative pathologies (Drug News Perspect., 2001, 14 (9), 568-76). For example, Lamotrigine, a sodium channel blocker and glutamate release inhibitor marketed in 1990 for the treatment of epilepsy has more recently been shown to be effective in the treatment of multiple sclerosis and has demonstrated neuroprotective effects in other neurodegenerative pathologies including ischemia. Another sodium channel blocker and glutamate release inhibitor, Riluzole, initially studied as an anticonvulsive agent, has been launched in 1996 for the treatment of amyotrophic lateral sclerosis. Although the results obtained with Riluzole in this pathology are modest, various other clinical studies relating to efficacy in the treatment of Parkinson's disease and Huntington's disease are ongoing. More recently developed blockers, with various levels of specificity towards voltage-dependent sodium and calcium channels, are undergoing study and have shown promising results as neuroprotectors (Mol. Pharmacol. 2006, 69 (1), 278-87). One recently developed sodium (brain type II) and calcium (N-type) channel blocker and glutamate release inhibitor, Sipatrigine, has shown optimal neuroprotective properties in various models, and is currently in phase II of a clinical trial for the treatment of cerebral ischemia. Phase III clinical trials on the treatment of Parkinson's disease are ongoing for the sodium and calcium channel blocker Sifanimide mesylate, while another two more recently discovered sodium channel blockers, Crobenetine and BW-534-U87, are in phase II trials for the treatment of cerebral ischemia. It is believed that such channel blockers act in this case by stabilising/modulating the sodium-dependent release of excitatory aminoacids (Glu, Asp) at the pre-synaptic level. Another role potentially played by said channel blockers is that of contributing towards cellular homeostasis and consequently inhibiting the "swelling" that inevitably precedes neuronal death. In this case, it is known that both NMDA receptor blockers, such as those of the sodium channels, are capable of preventing the neuronal "swelling" induced by hypoxia/reperfusion (Neuroscience, 2001, 103, 4, 971-83). Considered the extension of the inhibitory properties towards the neurodegenerative phenomena shown in numerous animal models by voltage-dependent sodium and calcium channel blockers, it is possible to also believe that other mechanisms, as yet unclear, besides those mentioned above, may play a role in the prevention of neurodegeneration. Hence, the search for novel molecules with neuroprotective activity through interaction with voltage-dependent sodium and calcium ion channels might offer interesting alternatives to the glutamatergic approach.

DESCRIPTION OF THE INVENTION

The present invention relates to compounds of formula (I), the pharmaceutically acceptable salts and/or solvates thereof, and their use in the preparation of speciality pharmaceuticals for the treatment of neurodegenerative pathologies such as cerebral ischemia, neurodegeneration induced by cranial trauma, Alzheimer's disease, Parkinson's disease, Multiple Sclerosis, Amyotrophic Lateral Sclerosis, the neurodegenerative phenomena resulting from trauma or viral infection. The compounds of formula (I) are represented by the following structure:

Compounds of Formula I:

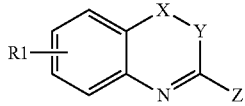

wherein:
X is a bond or methylene group (—CH$_2$—) or a sulphur atom (—S—)
Y is a methylene group (—CH$_2$—) or a sulphur atom (—S—)
Z is an amidine, thiourea or guanidine group as reported below Group Z:

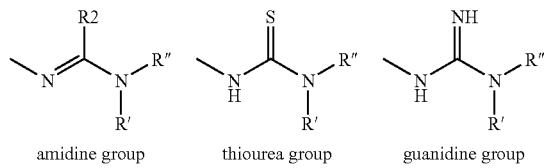

amidine group    thiourea group    guanidine group and wherein the R$_1$, R$_2$, R', R" substituents respectively are:
R$_1$ is a hydrogen (—H), fluorine (—F), chlorine (—Cl) atom, a methoxy (—OCH$_3$), trifluoromethoxy (—OCF$_3$), trifluoromethyl (—CF$_3$) or methanesulphonyl (—SO$_2$CH$_3$) group. The R$_1$ substituent may independently occupy the various positions available on the condensed phenyl; in a compound of formula (I) there is only a single R$_1$ substituent.
R$_2$ is a C$_1$-C$_4$ alkyl group such as methyl, ethyl, propyl, isopropyl, butyl, isobutyl, an optionally substituted cyclopropyl (—C$_3$H$_5$), methylcyclopropyl (—CH$_2$C$_3$H$_5$) or phenyl (—Ph) group or an optionally substituted benzyl (—CH$_2$Ph) group. Within the scope of the present invention, the term substituted phenyl or benzyl means the presence of no more than two substituents independently occupying the ortho, meta and para positions of the aromatic ring, selected independently from: fluorine (—F), chlorine (—Cl), methyl (—CH$_3$), methoxy (—OCH$_3$), hydroxyl (—OH), trifluoromethyl (—CF$_3$).
R' and R" are independently selected from: hydrogen (—H) and the groups defined above for R$_2$.
Provided that when X is a bond Y is never a methylene group (—CH$_2$—), thus excluding from the scope of the present invention the Δ-1-imidazolines corresponding to formula I, and provided that X and Y are not simultaneously a methylene group (—CH$_2$—), thus excluding from the scope of the present invention the 3,4-dihydroquinolines corresponding to formula I, or simultaneously a sulphur atom (—S—).

In accordance with this definition, when X is a bond and Y is an atom of sulphur (—S—), the compounds of formula (I) are amidines, thioureas or guanidines of substituted 2-aminobenzothiazoles:

X=bond, Y=S, compounds of Formula I:

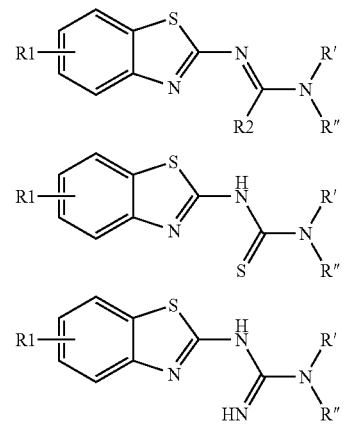

In this case, the scope of the present invention only relates to those compounds of formula (I) wherein the R$_1$ substituent occupies only positions 5 or 6 of the benzothiazole nucleus and provided R$_1$ is only: a trifluoromethoxy (—OCF$_3$), trifluoromethyl (—CF$_3$) or methanesulphonyl (—SO$_2$CH$_3$) group and provided that when Z is an amidine group, and R$_1$ is a —OCF$_3$ group or a —CF$_3$ group, R$_2$ is not a 2,6-difluorophenyl group and R' or R" are not an isopropyl group, a hydrogen atom, an unsubstituted phenyl or both are an ethyl and provided that when Z is a thiourea group and R', R" are a hydrogen atom and a 3-chloro-4-fluorophenyl group respectively, R$_1$ is not a methanesulphonyl (MeSO$_2$—) group occupying position 6 of the benzothiazole nucleus.

When X is a methylene (—CH$_2$—) group and Y is a sulphur atom (—S—), the compounds of formula (I) are amidines, thioureas or guanidines of 2-amino-4H-1,3-benzothiazine:

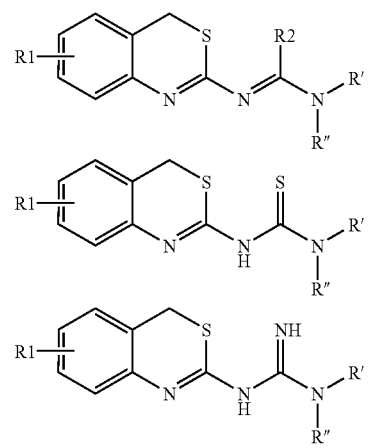

In this case, the scope of the present invention only includes those compounds of formula (I) wherein when R$_1$ and R' are simultaneously a hydrogen atom (—H), R" is not a: 4-methylphenyl, 3-chlorophenyl, 4-chlorophenyl group.

When X is a sulphur atom (—S—) and Y is a methylene group (—CH$_2$—), the compounds of formula (I) are substituted amidines, thioureas or guanidines of 3-amino-2H-1,4-benzothiazine:

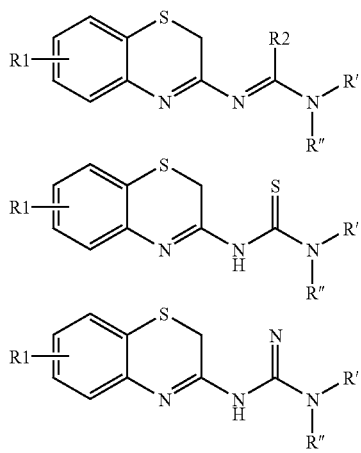

In this case, the scope of the present invention only relates to those compounds of formula (I) wherein: when $R_1$ is a chlorine atom at position -7, R' and R" are not simultaneously a hydrogen atom (—H), and when $R_1$ and R' are simultaneously a hydrogen atom (—H), R" is not phenyl (-Ph).

Representative but non-limiting examples of compounds of Formula (I) with regard to the scope of the present invention are reported below (see also Table 1 below):

N'[6-(trifluoromethoxy)benzothiazol-2-yl]acetamidine
N'[6-(trifluoromethoxy)benzothiazol-2-yl]acetamidine hydrochloride
N-methyl-N'[6-(trifluoromethoxy)benzothiazol-2-yl]acetamidine
N-methyl-N'[6-(trifluoromethoxy)benzothiazol-2-yl]acetamidine hydrochloride
N,N-dimethyl-N'-[6-(trifluoromethoxy)benzothiazol-2-yl]acetamidine
N,N-dimethyl-N'-[6-(trifluoromethoxy)benzothiazol-2-yl]acetamidine hydrochloride
N,N-diethyl-N'-[6-(trifluoromethoxy)benzothiazol-2-yl]acetamidine
N,N-dipropyl-N'-[6-(trifluoromethoxy)benzothiazol-2-yl]acetamidine
N'[6-(trifluoromethyl)benzothiazol-2-yl]acetamidine
N'[6-(methanesulphonyl)benzothiazol-2-yl]acetamidine
1-Methyl-3-[6-(trifluoromethoxy)benzothiazol-2-yl]thiourea
1-Ethyl-3-[6-(trifluoromethoxy)benzothiazol-2-yl]thiourea
1-Propyl-3-[6-(trifluoromethoxy)benzothiazol-2-yl]thiourea
1-Isopropyl-3-[6-(trifluoromethoxy)benzothiazol-2-yl]thiourea
1-Butyl-3-[6-(trifluoromethoxy)benzothiazol-2-yl]thiourea
1-Isobutyl-3-[6-(trifluoromethoxy)benzothiazol-2-yl]thiourea
1-Phenyl-3-[6-(trifluoromethoxy)benzothiazol-2-yl]thiourea
1-(4-fluorophenyl)-3-[6-(trifluoromethoxy)benzothiazol-2-yl]thiourea
1-Benzyl-3-[6-(trifluoromethoxy)benzothiazol-2-yl]thiourea
1-(4-fluorobenzyl)-3-[6-(trifluoromethoxy)benzothiazol-2-yl]thiourea
1-Methyl-3-[6-(trifluoromethyl)benzothiazol-2-yl]thiourea
1-Methyl-3-[6-(methanesulphonyl)benzothiazol-2-yl]thiourea
1-Ethyl-3-[6-(trifluoromethoxy)benzothiazol-2-yl]guanidine
1-Propyl-3-[6-(trifluoromethoxy)benzothiazol-2-yl]guanidine
N'-(4H-3,1-benzothiazin-2-yl)-N-methylacetamidine
N'-(4H-3,1-benzothiazin-2-yl)-N,N-dimethylacetamidine
N'-(4H-3,1-benzothiazin-2-yl)-N-ethylacetamidine
N'-(4H-3,1-benzothiazin-2-yl)-N-benzylacetamidine
N,N-diethyl-N'-[6-trifluoromethoxy-(4H-3,1-benzothiazin-2-yl)]-acetamidine
N,N-diethyl-N'-[7-trifluoromethoxy-(4H-3,1-benzothiazin-2-yl)]-acetamidine
N'-(4H-3,1-benzothiazin-2-yl)-N,N-dipropylacetamidine
N,N-dipropyl-N'-[6-trifluoromethoxy-(4H-3,1-benzothiazin-2-yl)]acetamidine
N,N-dipropyl-N'-[7-trifluoromethoxy-(4H-3,1-benzothiazin-2-yl)]-acetamidine
N'-(2H-1,4-benzothiazin-3-yl)-N-methylacetamidine
N'-(2H-1,4-benzothiazin-3-yl)-N,N-dimethylacetamidine
N'-(2H-1,4-benzothiazin-3-yl)-N-ethylacetamidine
N'-(2H-1,4-benzothiazin-3-yl)-N-benzylacetamidine
N'-(2H-1,4-benzothiazin-3-yl)-N,N-diethylacetamidine
N'-(2H-1,4-benzothiazin-3-yl)-N,N-dipropylacetamidine
1-(4H-3,1-benzothiazin-2-yl)-3-ethylthiourea
1-(4H-3,1-benzothiazin-2-yl)-3-propylthiourea
1-Ethyl-3-[6-(trifluoromethoxy)-4H-3,1-benzothiazin-2-yl]thiourea
1-Propyl-3-[6-(trifluoromethoxy)-4H-3,1-benzothiazin-2-yl]thiourea
1-(2H-1,4-benzothiazin-3-yl)-3-ethylthiourea
1-(2H-1,4-benzothiazin-3-yl)-3-propylthiourea
1-Ethyl-3-[7-(trifluoromethoxy)-2H-1,4-benzothiazin-3-yl]thiourea
(4H-3,1-benzothiazin-2-yl)-guanidine
1-Methyl-3-(4H-3,1-benzothiazin-2-yl)-guanidine
(2H-1,4-benzothiazin-3-yl)-guanidine
1-Methyl-3-(2H-1,4-benzothiazin-3-yl)-guanidine Structures for the representative compounds of Formula (I) are reported in Table 1,

TABLE 1

| Structure | Empirical formula | Molecular weight | Preparation of example No. |
|---|---|---|---|
| 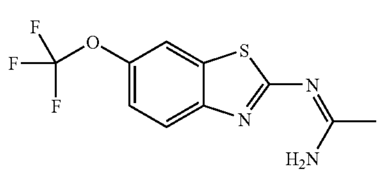 [SMILES: C/C(N)=N/c1nc2ccc(OC(F)(F)F)cc2s1] | C10H8F3N3OS | 275.25 | 1 |

TABLE 1-continued
| Structure | Empirical formula | Molecular weight | Preparation of example No. |
|---|---|---|---|
| 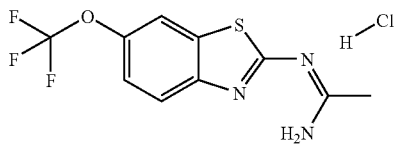 | C10H8F3N3OS · HCl | 312.75 | 2 |
| 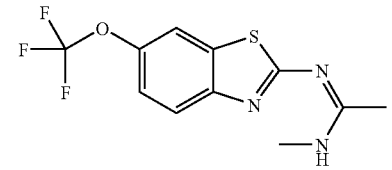 | C11H10F3N3OS | 289.28 | 3 |
| 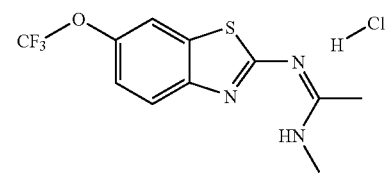 | C11H10F3N3OS · HCl | 325.5 | 4 |
| 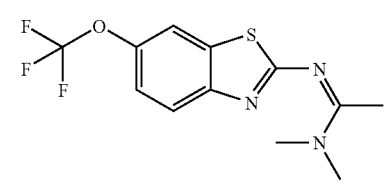 [SMILES: C/C(=N/c1nc2ccc(OC(F)(F)F)cc2s1)N(C)C] | C12H12F3N3OS | 303.31 | 5 |
| 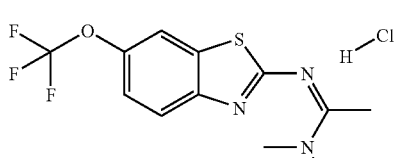 | C10H8F3N3OS · HCl | 339.84 | 6 |
| 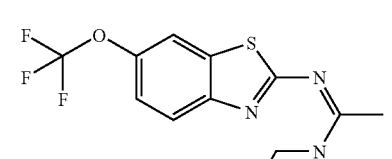 | C14H16F3N3OS | 331.36 | 7 |
| 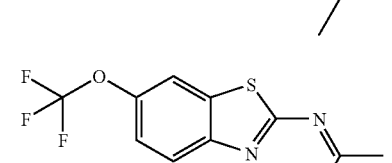 | C16H20F3N3OS | 359.42 | 8 |
| 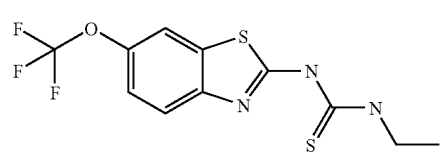 | C11H10F3N3OS2 | 321.35 | 9 |

TABLE 1-continued

| Structure | Empirical formula | Molecular weight | Preparation of example No. |
|---|---|---|---|
| | C12H12F3N3OS2 | 335.37 | 10 |
| | C12H12F3N3OS2 | 335.37 | 11 |
| | C13H14F3N3OS2 | 349.40 | 12 |
| | C13H14F3N3OS2 | 349.40 | — |
| 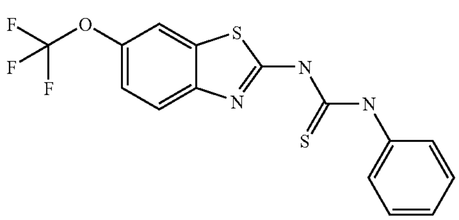 [SMILES: FC(F)(F)Oc1ccc2nc(NC(=S)Nc3ccccc3)sc2c1] | C15H10F3N3OS2 | 369.39 | 13 |
| 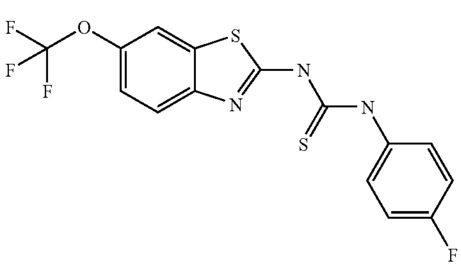 [SMILES: Fc1ccc(NC(=S)Nc2nc3ccc(OC(F)(F)F)cc3s2)cc1] | C15H9F4N3OS2 | 387.38 | 14 |
| 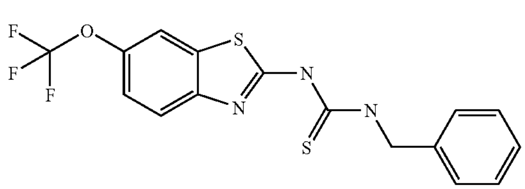 [SMILES: FC(F)(F)Oc1ccc2nc(NC(=S)NCc3ccccc3)sc2c1] | C16H12F3N3OS2 | 383.42 | — |
| 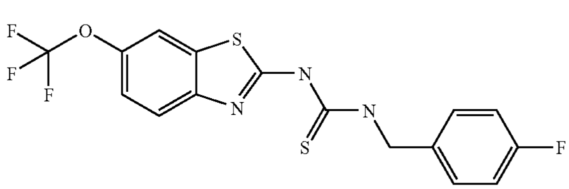 [SMILES: Fc1ccc(CNC(=S)Nc2nc3ccc(OC(F)(F)F)cc3s2)cc1] | C16H11F4N3OS2 | 401.41 | — |

TABLE 1-continued

| Structure | Empirical formula | Molecular weight | Preparation of example No. |
|---|---|---|---|
| 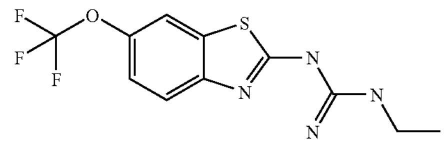 | C11H11F3N4OS | 304.30 | 15 |
| 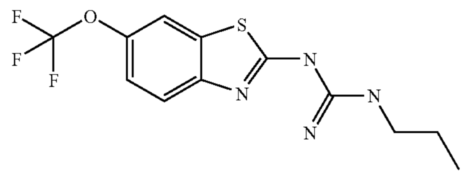 | C12H13F3N4OS | 318.32 | 16 |
| | C11H13N3S | 219.31 | 17 |
| | C12H15N3S | 233.34 | 18 |
| | C14H19N3S | 261.39 | — |
| 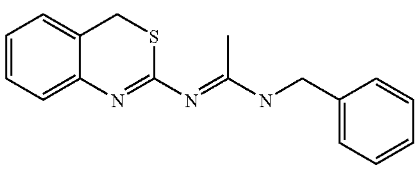 [SMILES: C/C(=N\C1=Nc2ccccc2CS1)NCc1ccccc1] | C17H17N3S | 295.41 | — |
| | C14H19N3S | 261.39 | 19 |
| 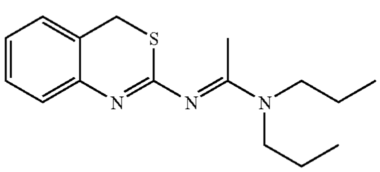 [SMILES: CCCN(CCC)/C(C)=N/C1=Nc2ccccc2CS1] | C16H23N3S | 289.45 | 20 |
| | C11H13N3S | 219.31 | 21 |
| | C12H15N3S | 233.34 | 22 |

TABLE 1-continued

| Structure | Empirical formula | Molecular weight | Preparation of example No. |
|---|---|---|---|
| 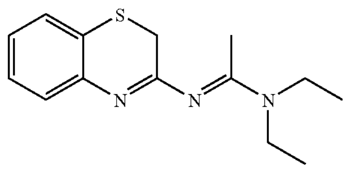 [SMILES: CCN(CC)/C(C)=N/C1=Nc2ccccc2SC1] | C14H19N3S | 261.39 | 23 |
| 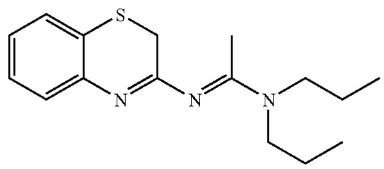 [SMILES: CCCN(CCC)/C(C)=N/C1=Nc2ccccc2SC1] | C16H23N3S | 289.45 | 24 |
| 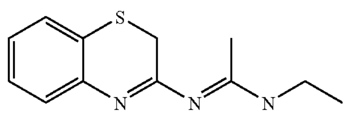 [SMILES: CCN/C(C)=N/C1=Nc2ccccc2SC1] | C12H15N3S | 233.34 | — |
| 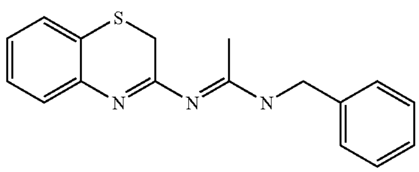 [SMILES: C/C(=N\C1=Nc2ccccc2SC1)NCc1ccccc1] | C17H17N3S | 295.41 | — |
| | C15H18F3N3OS | 345.39 | 25 |
| | C17H22F3N3OS | 373.44 | 26 |
| | C15H18F3N3OS | 345.39 | 27 |
| | C17H22F3N3OS | 373.44 | 28 |
| 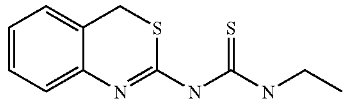 [SMILES: CCNC(=S)NC1=Nc2ccccc2CS1] | C11H13N3S2 | 251.37 | 29 |

TABLE 1-continued

| Structure | Empirical formula | Molecular weight | Preparation of example No. |
|---|---|---|---|
| 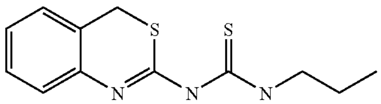 [SMILES: CCCNC(=S)NC1=Nc2ccccc2CS1] | C12H15N3S2 | 265.40 | 30 |
| | C12H12F3N3OS2 | 335.37 | 31 |
| | C13H14F3N3OS2 | 349.40 | 32 |
| | C12H12F3N3OS2 | 335.37 | 33 |
| | C13H14F3N3OS2 | 349.40 | 34 |
| | C9H10N4S | 206.27 | — |
| | C10H12N4S | 220.30 | — |
| | C9H10N4S | 206.27 | — |
| | C10H12N4S | 220.30 | — |

2-aminobenzothiazole amidines are compounds that have been known for some time, the antitubercular activity of alkyl- and aryl-amidines of 2-aminobenzothiazole derivatives has been known since 1962 (Misra Vinay S, J. Indian Chem. Soc., 1962, 39, 3, 208-2010), more recently, antiparasitic activity has been reported for analogous amidine derivatives (Philippe Raymond Loiseau, II Farmaco, 1990, 45, 9, 953-63) and their use as insecticides and acaricides has been claimed in EP 223141 (1987) and in PCT WO 9118882 (1991). Variously substituted amidines of 2-aminobenzothiazoles have been reported as synthetic intermediates of triazolo[5,1-b]benzothiazoles (Huey-Min Wang et al., Organic Preparations and Procedures International, 1996, 28, 3, 362-365) and several phenyl-amidine derivatives variously substituted at position 6 have been prepared by starting from the corresponding nitriles (Gorge Bratulescu et al., 2001, 52, 1-2, 63-67, Revista de Chemie, Bucharest, Romania); the synthesis of N,N-diaryl-amidines of 2-aminobenzothiazoles has been described with the scope of obtaining thiadiazolium salts (Kevin Pan et al., Synthetic Communications, 2003, 33, 12, 2053-2060). However, the potential neuroprotective activity and the use of amidine derivatives of 2-aminobenzothiazole in neurodegenerative pathologies such as cerebral ischemia, Alzheimer's disease, Parkinson's disease, Amyotrophic Lateral Sclerosis, neurodegenerative phenomena resulting from trauma or viral infection has not been described to date. Furthermore, amidine derivatives of 2-aminobenzothiazole, substituted with trifluoromethoxy (—OCF$_3$), trifluoromethyl (—CF$_3$), methanesulphonyl (—SO$_2$CH$_3$) groups at position 6 or 7 in the heterocyclic nucleus have not been described to date, with the exception of the following compounds: 2,6-difluoro-N-(1-methylethyl)-N'-[6-(trifluoromethoxy)-2-benzothiazolyl]-benzenecarboxylmidamide, RN: 110427-71-9, 2,6-difluoro-N-[6-(trifluoromethyl)-2-benzothiazolyl]-benzenecarboxylmidamide, RN: 110428-05-2, 2,6-difluoro-N-[6-(trifluoromethoxy)-2-benzothiazole]-benzenecarboxylmidamide, RN: 110428-06-3, N,N-diethyl-2,6-difluoro-N'-[6-(trifluoromethoxy)-2-benzothiazolyl]-benzenecarboxylmidamide, RN: 110428-07-4, 2,6-difluoro-N-phenyl-N'-[6-(trifluoromethoxy)-2-benzothiazolyl]-benzenecarboxylmidamide, RN: 110428-08-5, claimed as insecticides and acaricides in EP 223141 (1987).

The use of thiourea derivatives of 2-aminobenzothiazole as kinase inhibitors for oncology treatments has recently been reported in WO 2001057008, just as analogous derivatives have been described as having anti-inflammatory activity (JP 01003172 and Taniguchi Kiyoshi et al., Chemical & Pharmaceutical Bulletin 1993, 41, 2, 301-9) and antimicrobial activity (Abbas S. E. et al., Egyptian J. of Pharmaceutical Science, 1993, 34, 1-3, 195-205). Antitubercular activity has been reported for thioureas of 2-aminobenzothiazole (F. Russo, Bollettino Chimico Farmaceutico, 1961, 100, 252-6). The preparation of thioureas of 2-aminobenzothiazole by reaction with isothiocyanates has been described, just as their potential use as algaecides (Grish Chandra Singh et al., J. of Indian Chemical Society, 1968, 45, 1, 27-8); the preparation of various thioureas by reaction with $CS_2$ has been described (Tellez et al., European J. of Organic Chemistry, 2004, 20, 4203-4214). However, the neuroprotective activity and the use of thiourea derivatives of 2-aminobenzothiazole in neurodegenerative pathologies such as those mentioned above, has not been described to date. Furthermore, thiourea derivatives of 2-aminobenzothiazole, substituted with trifluoromethoxy (—$OCF_3$), trifluoromethyl (—$CF_3$), methanesulphonyl (—$SO_2CH_3$) groups at position 6 or 7 in the heterocyclic nucleus have not been described to date, with the exception of N-(3-chloro-4-fluorophenyl)-N'-[6-(methylsulphonyl)-2-benzothiazolyl]-Thiourea, RN: 941424-83-5, reported by CHEMCATS among the members of a library of commercial compounds.

Antibacterial activity has been described for guanidine derivatives of 2-aminobenzothiazoles (P. N. Bhargava et al., J. Medicinal Chemistry, 1969, 12, 558-9). The synthesis of guanidine derivatives of 2-aminobenzothiazoles, starting from the corresponding thioureas and amines in the presence of $PbO_2$, has been reported (P. N. Bhargava et al., Current Science, 1974, 43, 2, 33-6).

However, the neuroprotective activity and the use of guanidine derivatives of 2-aminobenzothiazole in neurodegenerative pathologies such as those mentioned above, has not been described to date. Furthermore, guanidine derivatives of 2-aminobenzothiazole, substituted with trifluoromethoxy (—$OCF_3$), trifluoromethyl (—$CF_3$), methanesulphonyl (—$SO_2CH_3$) groups at position 6 or 7 in the heterocyclic nucleus have not been described to date.

Amidine and guanidine derivatives of 2-amino-4H-1,3-benzothiazine have not been previously reported independently of the substituents present on the heterocyclic nucleus. Certain thiourea derivatives of 3-amino-4H-1,3-benzothiazine have been ascribed antiparasitic activity, as reported (P. N. Bhargava et al., Indian J. of Chemistry Section B: Organic Chemistry including Medicinal Chemistry, 1981, 20B, 6, 471-3) and specifically, the following are known: N-4H-3,1-benzothiazin-2-yl-N'-(4-methylphenyl)-thiourea, RN: 78959-50-9, N-4H-3,1-benzothiazin-2-yl-N'-(4-bromophenyl)-thiourea, RN: 78959-49-6, N-4H-3,1-benzothiazin-2-yl-N'-(4-chlorophenyl)-thiourea, RN: 78959-48-5, N-4H-3,1-benzothiazin-2-yl-N'-(3-chlorophenyl)-thiourea, RN: 78959-47-4.

Amidine and guanidine derivatives of 3-amino-2H-1,4-benzothiazine have not been previously reported independently of the substituents present on the heterocyclic nucleus. Thiourea derivatives of 3-amino-2H-1,4-benzothiazine have not previously been reported, with the exception of 1-[(2H-1,4-benzothiazin-3-yl)-3-phenyl]thiourea, RN: 101102-25-5 the synthesis of which is reported (Riolo Carla Bertoglio, Annali di Chimica, 1955, 45, 1174-7) and (7-chloro-2H-1,4-benzothiazin-3-yl)thiourea reported to have anti-inflammatory activity (P. N. Bhargava et al., Indian J. of Chemistry Section B: Organic Chemistry including Medicinal Chemistry, 1981, 20B, 6, 471-3).

Preparation of the Compounds of the Invention

Amidines of the compounds of Formula (I) are prepared starting from the corresponding 2-aminobenzothiazoles of Formula (II) by reacting with chloroimidates of formula (III) or by direct reaction with appropriately substituted amides of Formula (IV), in the presence of $POCl_3$ in toluene, as reported in Scheme 1, wherein the substituents have the same meaning as for the compounds of formula (I).

Scheme 1:

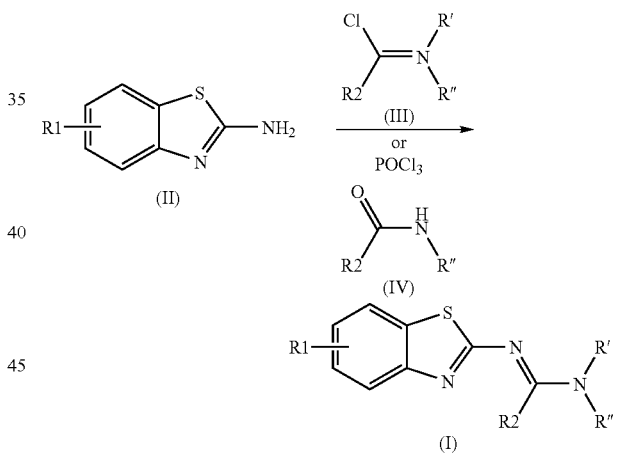

In compounds of formula (III) when R' or R" are other than (—H), the nitrogen atom is understood as being positively charged. Amidines of formula (I) wherein R'/R" are simultaneously a hydrogen atom (—H), may also be prepared by reacting appropriately substituted 2-aminobenzothiazole with the nitrile $R_2CN$ in the presence of anhydrous HCl or $AlCl_3$ as described for analogous products (Indian Journal of Heterocyclic Chemistry, 2001, 10(4), 315-316), or by reacting with the appropriate thioacetamide in acetone, similar to as described (Farmaco, 45(9), 953-63; 1990). Amidines of formula (I) wherein $R_2$ is an aryl or a higher alkyl and at least one of R' or R" is a hydrogen atom, may be prepared by reacting the appropriately substituted 2-thioaniline with a derivative of formula (V) as reported in Scheme 2, by refluxing in toluene, similar to as described (Tetrahedron, 60(19), 4315-4324; 2004).

Scheme 2

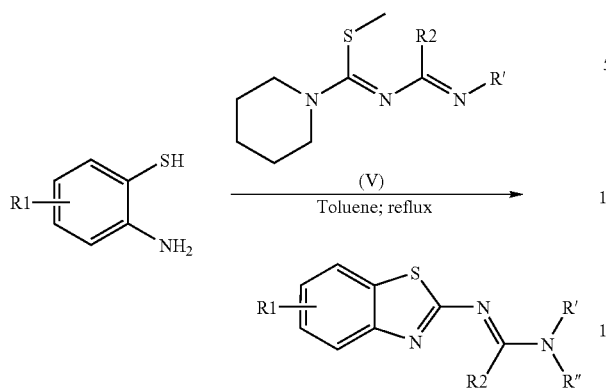

Other secondary amines may be used as an alternative to piperidine in the preparation reported according to Scheme 2. 2-aminobenzothiazoles of formula (II) substituted at positions 5 or 6 are compounds that are commercially available, or are prepared from the corresponding anilines using the methods reported below. 2-aminobenzothiazoles (II) are obtained from the corresponding anilines (VI) by reacting with ammonium thiocyanate, as reported in Scheme 3:

Scheme 3:

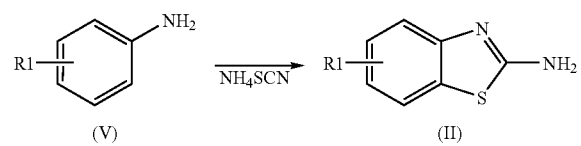

The reaction may be conducted in acetonitrile in the presence of benzyltrimethylammonium tribromide (similar to J. Organic Chemistry, 2003, 68, 8693). Alternatively, potassium thiocyanate may be used (similar to Journal of Medicinal Chemistry, 49(2), 664-677; 2006 see also Tetrahedron, 42(20), 5739-46; 1986). The reaction proceeds with good yield, both in the case where the aniline is 4-substituted and 3-substituted, giving rise to 6 and 5-substituted 2-aminobenzothiazoles respectively. 2-amino-6-trifluoromethoxybenzothiazole (RN: 850608-87-6) is a commercially available compound. 4-Trifluoromethylaniline (RN: 455-14-1), 3-trifluoromethylaniline (RN: 9-16-8), 4-methanesulphonylaniline (5470-49-5), 3-methansulphonylaniline hydrochloride (RN: 80213-28-1), 3-methanesulphonylaniline (RN: 352116-39-8), just like 4-trifluoromethoxy aniline (RN: 1535-73-5) are compounds that are commercially available. 3-Trifluoromethoxyaniline (RN: 1535-73-5) is prepared starting from 2-chlorophenol as described in *Bulletin de la Societe Chimique de France*, (6), 925-9; 1986. 3-Methanesulphonylaniline may also be prepared by nitration of the sulphone followed by reduction of the nitro group, as described in *Helvetica Chimica Acta* (1981), 64(6), 1849-53. 6-Methanesulphonyl-2-aminobenzothiazole may also be prepared by oxidation of the corresponding 6-thio-methylether-N-BOC-benzoimidazole obtained by reacting with thiocyanate as described above, starting from the commercially available compound 3-methylthioaniline (RN: 1783-81-9). Similar, the corresponding 5-methanesulphonyl-2-aminobenzothiazole may be obtained. The 2-aminobenzothiazoles substituted at positions 5 and 6, described in this invention, may also be obtained by reacting the appropriately substituted 2-thioanilines with bis-carboimidoyl-imidazole (RN: 104619-51-4), similar to as described in Journal of Heterocyclic Chemistry, 40(1), 191-193; 2003, as reported in Scheme 4:

Scheme 4:

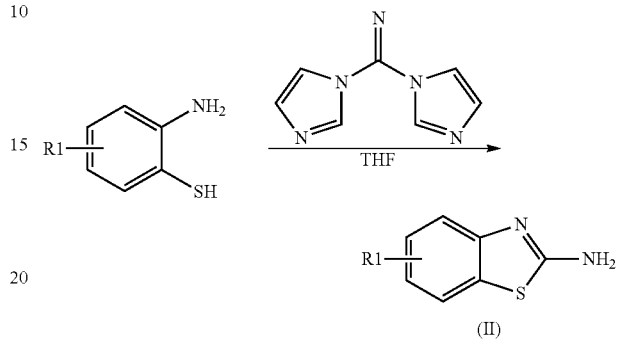

The 2-amino benzothiazoles substituted at positions 5 and 6 described in the present invention may be obtained alternatively by reacting appropriately substituted 2-thioanilines with para-toluenesulphonyl isonitrile, in the presence of sodium hydride, in THF. The sulphonylurea produced by electrophilic cyclisation is then hydrolysed in situ to give the 2-aminobenzothiazole derivative, similar to that described in Heterocycles (1997), 45(4), 745-755, as reported in Scheme 5:

Scheme 5:

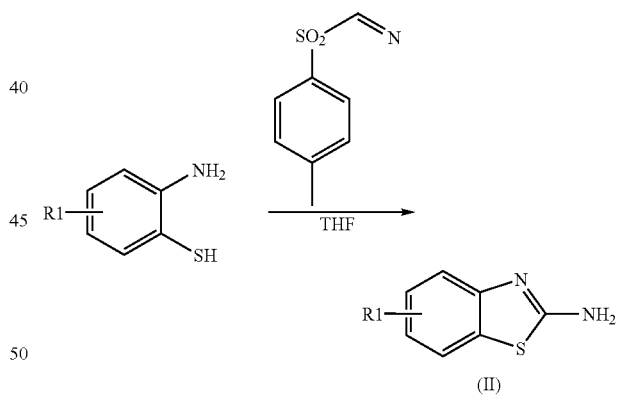

The appropriately substituted 2-thioanilines used in schemes 4 and 5 are obtained from the corresponding 2-chloroanilines by reacting them with sodium disulphide and sulphur in alcoholic solvents such as ethanol, similar to that described in Heterocyclic Communications, 10(1), 47-52; 2004 or Heterocyclic Communications, 6(1), 49-54, 2000.

Thioureas of 2-aminobenzothiazoles of formula (I), wherein at least one of the substituents R', R" is a hydrogen atom, are prepared by reacting the appropriately substituted 2-aminobenzothiazole of formula (II) with the isothiocyanate of formula (VII), as reported in Scheme 6, wherein the substituents have the same meanings as those described for the compounds of formula (I).

Scheme 6:

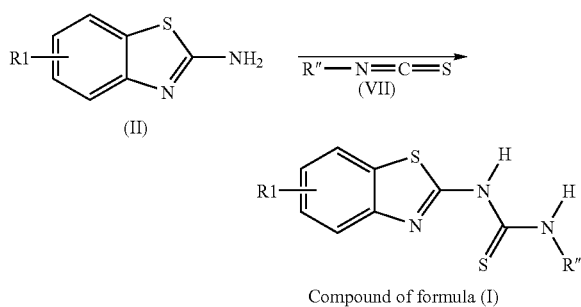

Compound of formula (I)

The aminobenzothiazoles of formula (II) are prepared as described above, the isothiocyanates of formula (VII) are commercially available products, or are prepared using known methods. The reaction is conducted in a solvent such as: ethanol, acetonitrile or toluene, at a temperature comprised of between room temperature and the reflux temperature of the solvent used, depending on the stability/reactivity of the corresponding isothiocyanate. Isothiocyanates that are not commercially available may be obtained from the corresponding amines by reacting them with carbon disulphide and carbodiimides such as dicyclohexylcarbodiimide, as described, for example, in J. Org. Chem. 1996, 61, 25, 8111-818.

Thioureas of 2-aminobenzothiazoles of formula (I) wherein the R' and R" substituents have the meanings reported for the compounds of formula (I), may be prepared by reacting the appropriately substituted 2-aminobenzothiazole of formula (II) with thiophosgene and the appropriate amine, as reported in Scheme 7, wherein the $R_1$ substituent has the same meaning as that described for the compounds of formula (I). Thiocarbonyldimidazole (TCDI) may be used as an alternative to thiophosgene.

Scheme 7

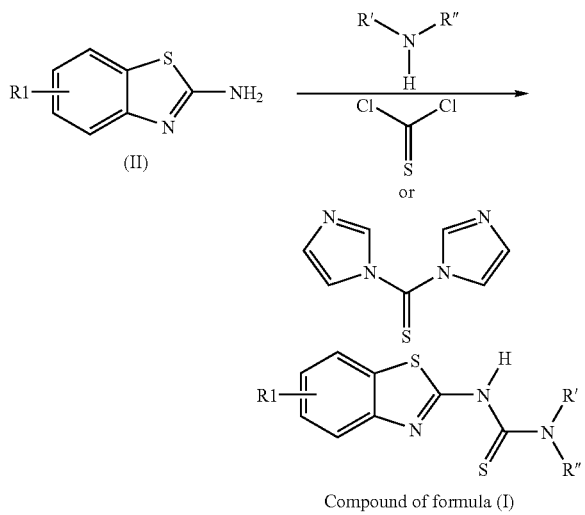

Compound of formula (I)

In the case where thiophosgene is used, the reaction may be conducted in acetonitrile as described for example in Bioorganic & Medicinal Chemistry, 12(15), 4189-4196; 2004.

Thiocarbonyldiimidazole as an equivalent to thiophosgene, and its use for the preparation of asymmetrical thioureas, has been originally described in Angew. Chem. Int. Ed. Engl. 1962, 1, 351. Bis(benzotriazolyl)-methanethione is a more recently described alternative to thiophosgene and TCDI, as reported by Katritzky (J. Org. Chem., 2004, 69, 2976-2982); this reagent, easily obtainable from thiophosgene and trimethylsilylbenzotriazole, is very useful for the attainment of thioureas where R' and R" are both sterically hindered alkyl residues or aromatic groups.

Guanidines of 2-aminobenzothiazoles of formula (I) are obtained by reacting the corresponding thioureas described in Scheme 8 with methyl iodide followed by reaction with ammonia:

Scheme 8

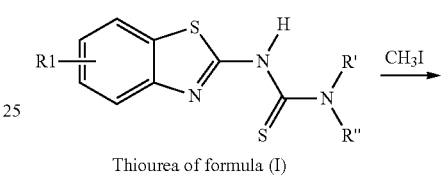

Thiourea of formula (I)

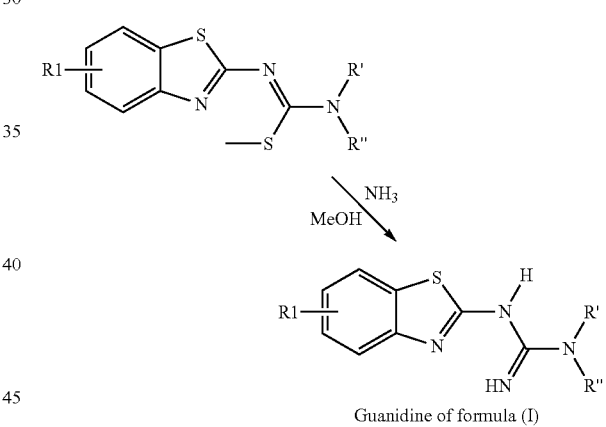

Guanidine of formula (I)

The reaction with methyl iodide may be conducted in acetone or in dichloromethane or dimethylformamide, while on the other hand, the subsequent reaction with ammonia is conducted in an alcoholic solvent, typically methanol or ethanol. Guanidines of 2-aminobenzothiazoles of formula (I) may also be obtained directly from 2-aminobenzothiazoles of formula (II) and amines HNR'R", according to a synthetic pathway analogous to that described in Scheme 8, but by direct reaction of the compound of formula (II) with $CS_2$ and $CH_3I$ in DMF, in the presence of NaOH and subsequent reaction with the amine in EtOH, similar to that reported in WO 0157008. Guanidines of 2-aminobenzothiazoles of formula (I) may also be obtained by reacting 2-aminobenzothiazoles of formula (II) and amines HNR'R" with methoxycarbonylisothiocyanate and methyl iodide, as exemplified in Scheme 9, in a manner analogous to that reported in Journal of Medicinal Chemistry, 31(5), 906-13; 1988.

Scheme 9

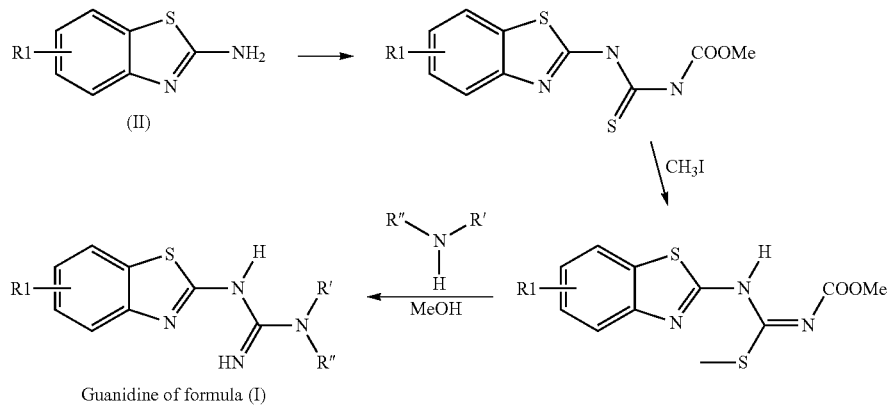

As an alternative to methyl iodide, thiourea can be activated with 1-ethyl-3-(3'-dimethylaminopropyl)carbodiimide hydrochloride (EDC), similar to that described in Bioorg. Med. Chem. Lett. 2004, 14, 5139.

Amidines, thioureas and guanidines of 3-amino-2H-1,4-benzothiazine and 2-amino-4H-3,1-benzothiazine are obtained by similarly applying the same methods as those detailed above for the case of the 2-aminobenzothiazoles. However, the amidines may be obtained from the amides or corresponding chloro-imidates as exemplified in Scheme 10, the nitrile $R_2CN$ in the presence of anhydrous HCl or $AlCl_3$. Amidines of formula (I), of 2-amino-4H-3,1-benzothiazine, wherein R' or R" is a hydrogen atom, may be prepared by reacting appropriately substituted 2-thiomethylaniline in a manner analogous to that reported in Scheme 2 for benzothiazoles.

The appropriately substituted 2-amino-4H-3,1-benzothiazine of formula (II), is prepared by starting from the corresponding 2-amino-benzylchloride or bromide by reacting with thiourea as reported in Scheme 11:

Scheme 10:

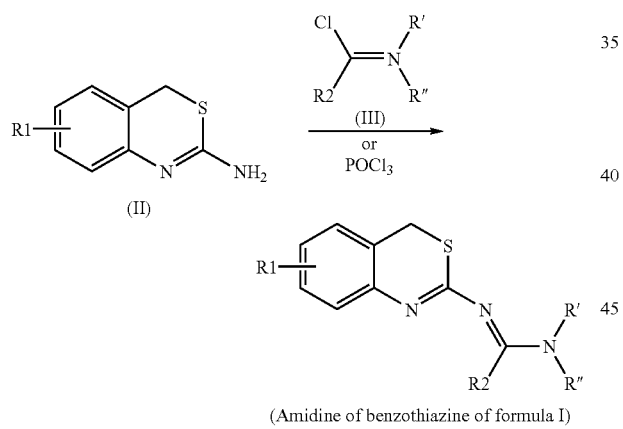

Scheme 11:

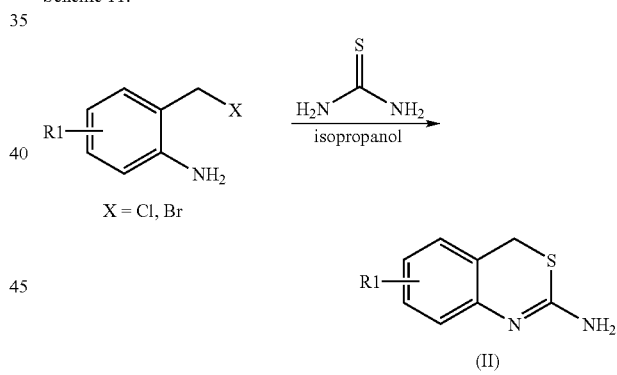

Alternatively, the 3-amino-1, 4-3H-benzothiazine of formula (II) may be prepared by starting from the aminothiophenol, as reported in Scheme 12. The reaction is conducted by starting from 2-aminothiophenol, appropriately substituted by alkylation, by means of phase transfer catalysis with chloroacetonitrile, the nitrile is subsequently cyclised by acid catalysis in an alcoholic solvent:

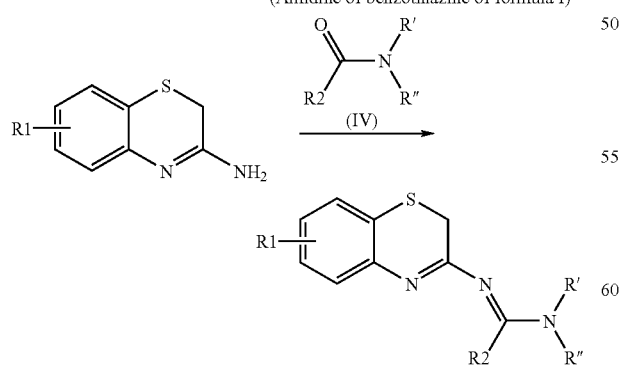

Amidines of formula (I) wherein R'/R" are simultaneously a hydrogen atom (—H), may also be prepared by reacting appropriately substituted 2 or 3-aminobenzothiazines with Scheme 12:

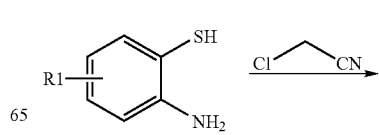

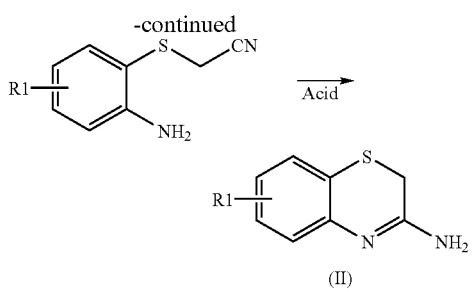

Substituted aminothiols are obtained as described above in the section relating to benzothiazoles.

Thioureas of 2-amino-4H-3,1-benzothiazine and 3-amino-2H-1,4-benzothiazine of formula (I), wherein at least one of R', R'' is a hydrogen atom (—H), are prepared by reacting the appropriately substituted 2-aminobenzothiazine of formula (II) with the isothiocyanate of formula (VII), as reported in Scheme 13, wherein the substituents have the same meaning as those described for the compounds of formula (I):

Schema 13:

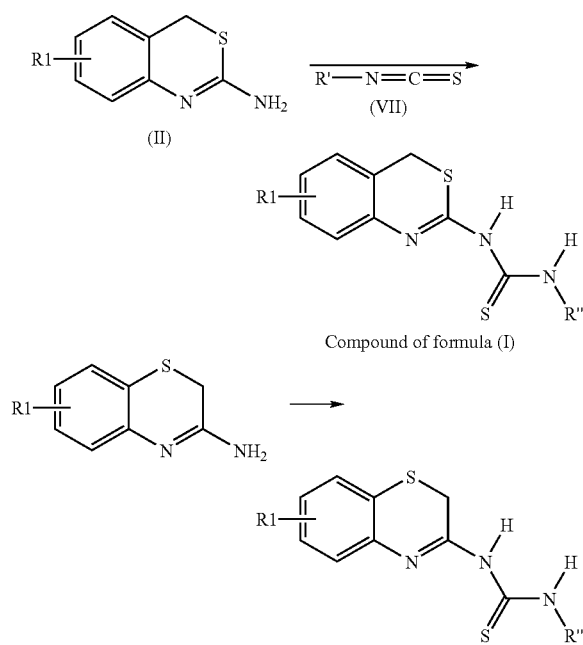

The amino-benzothiazines of formula (II) are prepared as described above, the isothiocyanates of formula (VII) are either commercially available products, or are prepared using known methods. The other methods for the preparation of substituted thioureas, described above for the amino-benzothiazoles, are similarly applicable to the preparation of analogous benzothiazine derivatives.

The guanidines of 2-amino-4H-3,1-benzothiazine and 3-amino-2H-1,4-benzothiazine of formula (I), besides being obtained as described above for the 2-aminobenzothiazoles of the thioureas by activation with EDC, can also be obtained from the corresponding 2 or 3-aminoderivatives by reacting with substituted cyanamides similar to that described in Bioorg. Med. Chem. Lett., 2003, 13, 107-110. The cyanamides that are not commercially available can be obtained by reacting the corresponding amine with cyanogen bromide in methanol, at 0° C. in the presence of $NaHCO_3$.

Examples of Preparation of the Compounds of the Invention

N'[6-(trifluoromethoxy)benzothiazol-2-yl]acetamidine

Example 1

Acetamide (0.47 mmol) is added to a solution of $POCl_3$ (0.85 mmol) in toluene (20 ml), chilled to 5-0° C., and the reaction mixture allowed to return to room temperature and then stirred for a further 30 minutes. 6-(trifluoromethoxy)-2-aminobenzothiazole (0.42 mmol), dissolved in toluene, is then added dropwise. On completion of addition, the reaction mixture is heated and refluxed for 6 hours, then cooled and poured into ice-water and basified using 1 N NaOH. The reaction mixture is extracted with $CHCl_3$, and washed with $H_2O$ until neutrality, then dried over $Na_2SO_4$, and concentrated. The crude product thus obtained is chromatographed through silica, eluting with petroleum ether/AcOEt (4:6). The product is obtained as a yellow oil, with yield: 67%. $^1$H-NMR ($CDCl_3$) δ ppm: 2.35 (s, 3H), 5.62 (br s, 2H), 7.20 (m, 2H), 7.48 (d, 1H, J=8.9). MS-ESI: m/z 276 (M+H$^+$).

N'-[6-(trifluoromethoxy)benzothiazol-2-yl]acetamidine hydrochloride

Example 2

To N'-[6-(trifluoromethoxy)benzothiazol-2-yl]acetamidine dissolved in methanol is added an HCl/ethyl ether saturated solution, dropwise with stirring, at 0° C. Ethyl ether is added to the acidic solution until it becomes lightly turbid, and the hydrochloride left to precipitate with gentle stirring, then filtered and washed with ethyl ether. White flakes, m.p. 202-206° C.

N-methyl-N'[6-(trifluoromethoxy)benzothiazol-2-yl]acetamidine

Example 3

Obtained as described in example 1, with a reflux time of 7 hours. Yellow solid (yield: 21%). $^1$H-NMR ($CDCl_3$) δ ppm: 2.21 (s, 3H), 3.11 (d, 3H, J=5.1), 7.18 (d, 1H, J=8.3), 7.58 (m, 2H), 10.68 (br s, 1H). MS-ESI: m/z 290 (M+H$^+$).

N-methyl-N'-[6-(trifluoromethoxy)benzothiazol-2-yl]acetamidine hydrochloride

Example 4

Obtained from methanol, as described in example 2, as pale yellow flakes, m.p. 202° C.

N,N-dimethyl-N'-[6-(trifluoromethoxy)benzothiazol-2-yl]acetamidine

Example 5

Obtained as described in example 1, with a reflux time of 1 hour. Pale yellow solid (34% yield). $^1$H-NMR ($CDCl_3$) δ ppm: 2.25 (s, 3H), 3.06 (s, 6H), 7.14 (d, 1H, J=8.7), 7.48 (s, 1H), 7.61 (d, 1H, J=8.8). MS-ESI: m/z 304 (M+H$^+$).

N,N-dimethyl-N'-[6-(trifluoromethoxy)benzothiazol-2-yl]acetamidine hydrochloride Example 6

Obtained from methanol, as described in example 2, as pale orange flakes, m.p. 219-222° C.

N,N-diethyl-N'-[6-(trifluoromethoxy)benzothiazol-2-yl]acetamidine

Example 7

Obtained as described in example 1, with a reflux time of 3 hours. Pale yellow oil (58% yield). $^1$H-NMR (CDCl$_3$): 1.21 (t, J=7.1, 6H), 2.31 (s, 3H), 3.49 (br s, 4H), 7.15 (d, J=8.8, 1H), 7.49 (s, 1H), 7.63 (d, J=8.8, 1H). MS (ESI): m/z 332 (M+H$^+$).

N,N-dipropyl-N'-[6-(trifluoromethoxy)benzothiazol-2-yl]acetamidine

Example 8

Obtained as described in example 1, with a reflux time of 3 hours. Yellow oil (52% yield).
$^1$H-NMR (CDCl$_3$): 0.92 (t, J=7.2, 6H), 1.66 (m, 4H), 2.30 (s, 3H), 3.36 (br d, 4H), 7.15 (d, J=9.0, 1H), 7.49 (s, 1H), 7.63 (d, J=8.9, 1H). MS (ESI): m/z 360 (M+H$^+$).

1-Ethyl-3-[6-(trifluoromethoxy)benzothiazol-2-yl]thiourea

Example 9

To a solution of 6-(trifluoromethoxy)-2-aminobenzothiazole (2.7 mmol) in toluene (20 ml) is added triethylamine (0.43 mmol) and ethylisothiocyanate (3.78 mmol). The resulting reaction mixture is heated and refluxed for 30 hours. The reaction mixture is cooled then evaporated and the residue diluted with CH$_2$Cl$_2$. The residue is washed with H$_2$O, dried over Na$_2$SO$_4$ then concentrated. The residue is chromatographed through silica gel, eluting with petroleum ether/AcOEt (65:35). Concentration of the appropriate fractions gives a solid that is then recrystallised from AcOEt/Et$_2$O, to give the desired product as pale yellow needles, m.p. 199-200° C. (36% yield). $^1$H-NMR (DMSO) 45 ppm: 1.17 (t, 3H, J=7.20), 3.55 (m, 2H), 7.37 (d, 1H, J=8.4), 7.70 (d, 1H, J=8.7), 8.02 (s, 1H), 9.54 (br s 2H). MS-ESI: m/z 320 (M–H$^+$).

1-Propyl-3-[6-(trifluoromethoxy)benzothiazol-2-yl]thiourea

Example 10

Obtained as yellow crystals, m.p. 226-228° C., 40% yield, as described in example 9, starting from 6-(trifluoromethoxy)-2-aminobenzothiazole and n-propylisothiocyanate, refluxed for 25 hours. $^1$H-NMR (DMSO) δ ppm: 0.90 (t, 3H, J=7.3), 1.57 (m, 2H), 3.48 (m, 2H), 7.35 (d, 1H, J=8.5), 7.79 (d, 1H, J=44.6), 8.01 (s, 1H), 9.62 (br s, 1H), 11.82 (br s, 1H). MS-ESI: m/z 334 (M–H$^+$).

1-Isopropyl-3-[6-(trifluoromethoxy)benzothiazol-2-yl]thiourea

Example 11

Obtained as white crystals, m.p. 242° C., 23% yield, as described in example 9, starting from 6-(trifluoromethoxy)-2-aminobenzothiazole and iso-propylisothiocyanate, refluxed for 54 hours. $^1$H-NMR (DMSO) δ ppm: 1.21 (d, 6H, J=6.0), 4.33 (m, 1H), 7.33 (d, 1H, J=8.6), 7.69 (d, 1H, J=8.5), 7.99 (s, 1H), 9.36 (br s, 1H), 11.70 (br s, 1H). MS-ESI: m/z 334 (M–H$^+$).

1-Butyl-3-[6-(trifluoromethoxy)benzothiazol-2-yl]thiourea

Example 12

Obtained as white crystals, m.p. 211° C., 27% yield, as described in example 9, starting from 6-(trifluoromethoxy)-2-aminobenzothiazole and n-butylisothiocyanate, refluxed for 52 hours. $^1$H-NMR (DMSO) δ ppm: 0.88 (t, 3H, J=7.2), 1.33 (m, 2H), 0.92 (m, 2H), 3.50 (m, 2H), 7.33 (d, 1H, J=8.5), 7.66 (d, 1H, J=8.5), 7.98 (s, 1H), 9.53 (br s, 1H), 11.80 (br s, 1H). MS-ESI: m/z 348 (M–H$^+$).

1-Phenyl-3-[6-(trifluoromethoxy)benzothiazol-2-yl]thiourea

Example 13

Obtained as white crystals, m.p. 234° C., 22% yield, as described in example 9, starting from 6-(trifluoromethoxy)-2-aminobenzothiazole and phenylisothiocyanate, refluxed for 30 hours. $^1$H-NMR (DMSO) δ ppm: 7.15 (m, 1H), 7.33 (m, 3H), 7.63 (m, 3H), 7.98 (s, 1H), 10.76 (br s, 2H). MS-ESI: m/z 368 (M–H$^+$).

1-(4-Fluorophenyl)3-[6-(trifluoromethoxy)benzothiazol-2-yl]thiourea

Example 14

Obtained as pale yellow crystals, m.p. 207° C., 20% yield, as described in example 9, starting from 6-(trifluoromethoxy)-2-aminobenzothiazole and 4-fluorophenylisothiocyanate, refluxed for 42 hours. $^1$H-NMR (DMSO) δ ppm: 7.14 (m, 2H), 7.40 (m, 1H), 7.62 (m, 3H), 7.97 (s, 1H), 10.72 (br s, 21-1). MS-ESI: m/z 386 (M–H$^+$).

1-Ethyl-3-[6-(trifluoromethoxy)benzothiazol-2-yl]guanidine

Example 15

To a solution of 1-Ethyl-3-[6-(trifluoromethoxy)benzothiazol-2-yl]thiourea (example 9) (0.76 mmol) in acetone (40 ml) is added methyl iodide (0.84 mmol), at room temperature and under an atmosphere of nitrogen. On completion of the reaction, the mixture is evaporated under reduced pressure, and the residue dissolved in methanol. The solution is cooled in ice and saturated with gaseous NH$_3$, then allowed to return to room temperature and stirred overnight. The solution is then concentrated, diluted with CH$_2$Cl$_2$, washed with H$_2$O, anhydrated over Na$_2$SO$_4$ and then concentrated. The residue is purified by chromatography through silica, eluting with hexane/Et$_2$O (65:35). The product obtained by combining the appropriate fractions is recrystallised from hexane/ Et$_2$O to give the desired product as white crystals, m.p. 127-129° C., 20% yield. $^1$H-NMR (CDCl$_3$) δ ppm: 1.27 (m, 3H), 3.28 (m, 2H), 6.28 (br s, 3H), 7.11 (d, 1H, J=8.9), 7.24 (s, 1H), 7.47 (d, 1H, J=8.8). MS-ESI: m/z 304 (M+H$^+$).

1-Propyl-3-[6-(trifluoromethoxy)benzothiazol-2-yl] guanidine

Example 16

Obtained as described in example 15 by starting from 1-Propyl-3-[6-(trifluoromethoxy)benzothiazol-2-yl]thiourea, Example 10, with a yield of 22%, as white needles, m.p. 110-111° C. $^1$H-NMR (CDCl$_3$) δ ppm: 1.03 (t, 3H, J=7.4), 1.70 (m, 2H), 3.19 (q, 2H, J=6.2), 6.22 (br s, 3H), 7.11 (d, 1H, J=7.2), 7.24 (s, 1H), 7.46 (d, 1H, J=8.8). MS-ESI: m/z 319 (M+H$^+$).

2-Amino-6-(trifluoromethoxy)-benzothiazole

To a mixture of 4-trifluoromethoxyaniline (2.07 mmol) and ammonium thiocyanate (2 mmol) in acetonitrile, is added benzyltrimethylammonium tribromide, at room temperature. The reaction is left to proceed while stirring at room temperature for 24 hours; it is then neutralised with NaHCO$_3$ and extracted with CH$_2$Cl$_2$. The combined organic extracts are washed with H$_2$O, dried over Na$_2$SO$_4$, filtered and then evaporated under vacuum. The crude product is purified by chromatography through silica, eluting with petroleum ether/AcOEt (1:1), and a solid obtained that is recrystallised from hexane/ethyl ether to give 2-amino-6-(trifluoromethoxy)-benzothiazole as pale yellow flakes, with a yield of 80%.

2-Amino-6-(trifluoromethoxy)-benzothiazole hydrochloride

To a solution of 2-amino-6-(trifluoromethoxy)-benzothiazole in methanol (10 ml) is added 37% HCl (1 ml) dropwise, and the precipitate recrystallised from methanol to give quantitative yield of the hydrochloride, as white needles, m.p.: 214-216° C.

2-Amino-4H-3,1-benzothiazine 2-aminobenzylalcohol (2.0 g, 16 mmol) in conc. HCl (10 ml) is heated at 100° C. for 15 minutes in a sealed vial, the resulting precipitate is filtered, washed with diethyl ether to give a white solid which is dissolved in isopropanol (20 ml) and treated with thiourea. The resulting reaction mixture is refluxed for 20 hours then concentrated, and the residue taken up with H$_2$O and basified with 2 N NaOH. The basic solution thus obtained is extracted with CH$_2$Cl$_2$. The organic extracts are combined, washed with H$_2$O, dried over Na$_2$SO$_4$ and then concentrated. The residue is purified by chromatography through silica, eluting with petroleum ether/AcOEt (1:1), and then recrystallised from EtOH to give the desired product as a pale yellow solid, m.p. 132-135° C., with a yield of 64%. $^1$H-NMR (CDCl$_3$): 3.90 (s, 2H), 5.09 (br s, 2H), 7.00-7.12 (m, 3H) 7.20-7.28 (m, 1H). 165 (M+H$^+$). The compound is more stable as the oxalate salt, m.p. 178-182° C., prepared by precipitation with oxalic acid.

2-Amino-6-trifluoromethoxy-4H-3,1-benzothiazine

Concentrated HCl (4 ml) is added slowly to a solution of N-[2-hydroxymethyl-4-(trifluoromethoxy)phenyl]-pivaloylamide (0.35 g, 1.2 mmol) in dioxane (3 ml) and the resulting reaction mixture heated at 80° C. for 4 hours, then diluted with isopropanol (20 ml), and thiourea (0.14 g, 1.8 mmol) added and the mixture refluxed for 20 hours. The solvent is then evaporated under vacuum and the residue diluted with H$_2$O, basified with 2 N NaOH, and extracted with CH$_2$Cl$_2$. The combined organic extracts are dried over Na$_2$SO$_4$ and concentrated under vacuum. The residue is purified by chromatography through silica, eluting with AcOEt/petroleum ether (1:1). The product is obtained as a yellow solid, with a yield of 84%. Recrystallisation from EtOH gives a solid with m.p. 115-118° C. $^1$H-NMR (CDCl$_3$): 3.87 (s, 2H), 5.16 (br s, 2H), 6.97-7.11 (m, 3H). MS (ESI): m/z 249 (M+H$^+$).

N-[2-hydroxymethyl-4-(trifluoromethoxy)phenyl]-pivaloylamide

To a solution of N-[2-Formyl-4-(trifluoromethoxy)phenyl]-pivaloylamide (1.2 g, 4.1 mmol) in absolute EtOH (20 ml), chilled to 0° C., is added, in batches and with stirring, NaBH$_4$ (0.19 g, 4.9 mmol). The reaction mixture is stirred for 15 minutes at 0° C. and then at room temperature for a further 30 minutes, then concentrated, and the residue diluted with H$_2$O and extracted with CHCl$_3$: The combined organic extracts are dried over Na$_2$SO$_4$ and concentrated to give the product as a colourless solid (1.2 g, 90% yield). Crystallisation from hexane gives a solid with m.p. 71-73° C. $^1$H-NMR (CDCl$_3$): 1.30 (s, 9H), 2.24 (t, J=5.9, 1H), 4.68 (d, J=5.9, 2H), 7.03 (m, 1H), 7.16 (m, 1H), 8.15 (d, J=8.9, 1H), 8.86 (br s, 1H). MS (ESI): m/z 315 (M+Na$^+$).

N-[2-Formyl-4-(trifluoromethoxy)phenyl]-pivaloylamide

A solution of t-butyl lithium in pentane (1.7 M) (8.1 ml, 13.9 mmol) is added dropwise to N-[4-(trifluoromethoxy)phenyl]-pivaloylamide (1.5 g, 5.7 mmol) in THF (50 m) at −75° C. After one hour, DMF (0.44 ml, 5.7 mmol) is added with stirring, without the temperature exceeding −75° C., and the reaction mixture then stirred at −75° C. for a further 45 minutes. The refrigerant is removed and the mixture allowed to reach room temperature then stirred for a further 20 minutes at room temperature, then poured into ice-water. The organic phase is washed with 4 N HCl and then with a saturated solution of NaCl, dried over Na$_2$SO$_4$ and then concentrated. The residue is purified by chromatography through silica, eluting with CH$_2$Cl$_2$/petroleum ether (1:1). The product is obtained as a colourless oil, with a yield of 72%.
$^1$H-NMR (CDCl$_3$): 1.34 (s, 9H), 7.43-7.50 (m, 2H), 8.86 (d, J=9.0, 1H), 9.90 (s, 1H), 11.30 (br s, 1H), MS (ESI): m/z 290 (M+H$^+$).

N-[4-(Trifluoromethoxy)phenyl]-pivaloylamide

To a solution of 4-(trifluoromethoxy)-aniline (1.0 g, 5.6 mmol) and triethylamine (0.71 ml, 5.1 mmol) in CH$_2$Cl$_2$ (15 ml), chilled to 0° C., is added dropwise pivaloyl chloride (0.73 ml, 5.9 mmol), and the reaction mixture then stirred at room temperature for 18 hours. The mixture is then poured into ice-water and extracted with CH$_2$Cl$_2$. The combined organic extracts are dried over Na$_2$SO$_4$ then concentrated, and the solid obtained is recrystallised from hexane to give the product as colourless needles, m.p. 104-107° C. $^1$H-NMR (CDCl$_3$): 1.30 (s, 9H), 7.15 (d, J=8.8, 2H), 7.33 (br s, 1H), 7.53 (d, J=9.2, 2H). MS (ESI): m/z 262 (M+H$^+$).

N'-(4H-3,1-benzothiazin-2-yl)-N-methylacetamidine

Example 17

To a mixture of POCl$_3$ (4.9 mmol) in toluene (20 ml), chilled to 0° C., is added acetamide (2.7 mmol), while stirring under an atmosphere of inert gas, and the mixture is then stirred at room temperature for 30 minutes and 2-amino-4H-3,1-benzothiazine (2.4 mmol) added. The reaction mixture is heated and refluxed for 3 hours, cooled and poured into ice-water, then basified with 2 N NaOH and extracted with CHCl$_3$. The organic phase is washed with H$_2$O, dried over Na$_2$SO$_4$ and concentrated to give a residue which is purified through silica gel, eluting with AcOEt. Concentration of the appropriate fractions gives a yellow solid, with a yield of 40%. $^1$H-NMR (CDCl$_3$): 2.16 (s, 3H), 3.04 (s, 3H), 3.94 (s, 2H), 7.00-7.08 (m, 3H), 7.17-7.024 (m, 1H), 11.90 (br s, 11-1). MS (ESI): m/z 220 (M+H$^+$). The product is then converted into the corresponding oxalate salt, m.p. 110-113° C. dec.

N'-(4H-3,1-benzothiazin-2-yl)-N,N-dimethylacetamidine

Example 18

Similar to that described for example 17, the product is obtained with a yield of 63%, using N,N-dimethylacetamide in place of acetamide. $^1$H-NMR (CDCl$_3$): 2.20 (s, 3H), 3.06 (s, 6H), 3.99 (s, 2H), 7.06-7.12 (m, 2H), 7.16-7.27 (m, 2H). MS (ESI): m/z 234 (M+H$^+$). The corresponding oxalate has an m.p. of 154-157° C. dec.

N'-(4H-3,1-benzothiazin-2-yl)-N,N-diethylacetamidine

Example 19

Similar to that described for example 17, the product is obtained with a yield of 38%, using N,N-diethylacetamide in place of acetamide, and eluting with petroleum ether/AcOEt (1:1). Yellow oil, $^1$H-NMR (CDCl$_3$): 1.18 (t, J=7.2, 6H), 2.19 (s, 3H), 3.42 (br s, 4H), 3.97 (s, 2H), 7.01-7.07 (m, 2H), 7.14-7.27 (m, 2H). MS (ESI): m/z 262 (M+H$^+$).

N'-(4H-3,1-benzothiazin-2-yl)-N,N-dipropylacetamidine

Example 20

Similar to that described for example 17, the product is obtained with a yield of 54%, using N,N-dipropylacetamide in place of acetamide, and eluting with petroleum ether/AcOEt (1:1). Yellow oil, $^1$H-NMR (CDCl$_3$): 0.91 (t, J=7.4, 6H), 1.61 (m, 4H), 2.19 (s, 3H), 3.29 (br s, 4H), 3.98 (s, 2H), 7.06-7.08 (m, 2H), 7.16-7.25 (m, 2H). MS (ESI): m/z 290 (M+H$^+$).

N'-(2H-1,4-benzothiazin-3-yl)-N-methylacetamidine

Example 21

Similar to that described in example 17, the product is obtained with a yield of 28% using 3-amino-2H-1,4-benzothiazine in place of 2-amino-4H-3,1-benzothiazine, and eluting with AcOEt/TEA (9:1). Yellow solid $^1$H-NMR (CDCl$_3$): 2.16 (s, 3H), 3.05 (s, 3H), 3.29 (s, 2H), 6.92-7.27 (m, 4H), 12.50 (br s, 1H). MS (ESI): m/z 220 (M+H$^+$). Oxalate m.p. 164-166° C. dec.

N'-(2H-1,4-benzothiazin-3-yl)-N,N-dimethylacetamidine

Example 22

Similar to that described in example 17, the product is obtained with a yield of 26% using 3-amino-2H-1,4-benzothiazine and N,N-dimethylacetamide, eluting with AcOEt/triethylamine (95:5). Colourless oil, $^1$H-NMR (CDCl$_3$): 2.24 (s, 3H), 3.05 (s, 6H), 3.19 (s, 2H), 6.90-6.97 (m, 1H), 7.07-7.27 (m, 3H). MS (ESI): m/z 234 (M+H$^+$). Oxalate m.p. 120-122° C. dec.

N'-(2H-1,4-benzothiazin-3-yl)-N,N-diethylacetamidine

Example 23

Similar to that described in example 17, the product is obtained with a yield of 16% using 3-amino-2H-1,4-benzothiazine and N,N-diethylacetamide. Colourless oil, $^1$H-NMR (CDCl$_3$): 1.18 (t, J=7.9, 6H), 2.26 (s, 3H), 3.18 (s, 2H), 3.44 (br s, 4H), 6.89-6.97 (m, 1H), 7.10-7.27 (m, 3H). MS (ESI): m/z 262 (M+H$^+$).

N'-(2H-1,4-benzothiazin-3-yl)-N,N-dipropylacetamidine

Example 24

Similar to that described in example 17, the product is obtained with a yield of 9% using 3-amino-2H-1,4-benzothiazine and N,N-dipropylacetamide. Dark oil, $^1$H-NMR (CDCl$_3$): 0.91 (t, J=7.4, 6H), 1.63 (m, 4H), 2.26 (s, 3H), 3.23-3.29 (m, 6H), 6.89-6.97 (m, 1H), 7.07-7.27 (m, 3H). MS (ESI): m/z 290 (M+H$^+$).

N,N-diethyl-N'-[6-(trifluoromethoxy)-4H-3,1-benzothiazin-2-yl]acetamidine

Example 25

Similar to that described for example 17, the product is obtained with a yield of 65%, using 2-amino-6-trifluoromethoxy-4H-3,1-benzothiazine, and eluting with petroleum ether/AcOEt (1:1). Yellow oil (65% yield). $^1$H-NMR (CDCl$_3$): 1.24 (t, J=7.3, 6H), 2.19 (s, 3H), 3.39 (br s, 4H), 3.95 (s, 2H), 6.95 (s, 1H), 7.04-7.18 (m, 2H). MS (ESI): m/z 346 (M+H$^+$).

N,N-dipropyl-N'-[6-(trifluoromethoxy)-4H-3,1-benzothiazin-2-yl]acetamidine

Example 26

Similar to that described for example 17, the product is obtained with a yield of 58%, using 2-amino-6-trifluoromethoxy-4H-3,1-benzothiazine and N,N-dipropylacetamide, and eluting with petroleum ether/AcOEt (65:35). Yellow oil, $^1$H-NMR (CDCl$_3$): 0.89 (t, J=7.3, 6H), 1.61 (m, 4H), 2.13 (s, 3H), 3.30 (br d, 4H), 3.93 (s, 2H), 6.93 (m, 1H), 7.04 (d, J=9.6, 1H), 7.15 (d, J=8.7, 1H). MS (ESI): m/z 374 (M+H$^+$).

N,N-diethyl-N'-[7-(trifluoromethoxy)-2H-1,4-benzothiazin-3-yl]acetamidine

Example 27

Similar to that described in example 17, the product is obtained with a yield of 34% using 3-amino-7-trifluoromethoxy-2H-1,4-benzothiazine. Yellow oil, $^1$H-NMR (CDCl$_3$): 1.19 (t, J=7.1, 6H), 2.27 (s, 3H), 3.18 (s, 2H), 3.25-3.47 (m, 4H), 6.96 (m, 1H) 7.11-7.20 (m, 2H). MS (ESI): m/z 346 (M+H$^+$).

3-amino-2H-1,4-benzothiazine

A mixture of 2-aminothiophenol (1.6 ml, 15 mmol) in 25% NaOH (10 ml) and chloroacetonitrile (0.95 ml, 15 mmol) in CH$_2$Cl$_2$ (20 ml) is stirred at room temperature for 20 hours, in the presence of tetrabutylammonium hydrogensulphate (0.51 g, 1.5 mmol). The organic phase is then separated, washed with H$_2$O, dried over Na$_2$SO$_4$ and concentrated. The residue is taken up with 5% HCl/EtOH (20 ml) and the resulting solution refluxed for 2 hours. The solvent is evaporated under vacuum and the resulting solid taken up in H$_2$O then washed with CHCl$_3$, basified with NH$_4$OH and the precipitate obtained extracted with CHCl$_3$. The organic phase is dried over Na$_2$SO$_4$ and concentrated. The residue is purified by chromatography through silica, eluting with AcOEt/Triethylamine (8:2). The product is obtained as a yellowish solid, with a yield of 32%. Recrystallisation from ethyl acetate gives the product with an m.p. of 168-172° C., $^1$H-NMR (CDCl$_3$): 3.18 (s, 2H), 4.38 (br s, 2H), 6.89-7.25 (m, 4H). MS (ESI): m/z 165 (M+H$^+$). MS (ESI): m/z 165 (M+H$^+$). The product is more stable as the oxalate salt, white solid m.p. 182-184° C.

3-Amino-7-trifluoromethoxy-2H-1,4-benzothiazine

A solution of 2-[2-amino-5-(trifluoromethoxy)phenylthio]-acetonitrile (0.70 g, 2.82 mmol) in 5% EtOH/HCl (20 ml) is refluxed for 2 hours. The solvent is then evaporated under vacuum and the residue diluted with H$_2$O. The resulting aqueous solution is washed with CHCl$_3$, basified with conc. NH$_4$OH and the precipitate extracted with CHCl$_3$. The combined organic extracts are dried over Na$_2$SO$_4$ and concentrated to give the product as a pale yellow solid (0.45 g, 64% yield, m.p. 94-96° C.). $^1$H-NMR (CDCl$_3$): 3.14 (s, 2H), 5.04 (br s, 2H), 6.92-7.10 (m, 3H). MS (ESI): m/z 249 (M+H$^+$).

2-[2-amino-5-(trifluoromethoxy)phenylthio]-acetonitrile

A suspension of 2-amino-6-trifluoromethoxybenzothiazole (1.8 g, 7.7 mmol) in 10 N NaOH (30 ml) is refluxed, under a current of nitrogen, for 2 hours, after which time the suspension becomes a clear solution, and to which chloroacetonitrile (0.48 ml, 7.7 mmol) in CH$_2$Cl$_2$ (50 ml) and tetrabutylammonium hydrogensulphate (0.26 g, 0.77 mmol) are added. The resulting reaction mixture is stirred for 18 hours at room temperature, then the organic phase is separated, washed with water and dried over Na$_2$SO$_4$. The solvent is evaporated and the residue chromatographed through silica, eluting with petroleum ether/AcOEt (1:1) to give the product as a dark oil (1.1 g, 58% yield). $^1$H-NMR (CDCl$_3$): 3.45 (s, 2H), 4.44 (br s, 2H), 6.74 (d, J=8.8, 1H), 7.10 (m, 1H), 7.39 (m, 1H). MS (ESI): m/z 249 (M+H$^+$).

N,N-dipropyl-N'-[7-(trifluoromethoxy)-2H-1,4-benzothiazin-3-yl]acetamidine

Example 28

Similar to that described for example 17, the product is obtained with a yield of 62%, using 3-amino-7-trifluoromethoxy-2H-1,4-benzothiazine and N,N-dipropylacetamide, and eluting with petroleum ether/AcOEt. Orange oil, $^1$H-NMR (CDCl$_3$): 0.91 (t, J=7.3, 6H), 1.63 (m, 4H), 2.25 (s, 3H), 3.17-3.48 (m, 6H), 6.95 (d, J=8.9, 1H), 7.11-7.20 (m, 2H). MS (ESI): m/z 374 (M+H$^+$).

1-(4H-3,1-benzothiazin-2-yl)-3-ethylthiourea

Example 29

Ethylisothiocyanate (0.84 mmol) is added dropwise to a solution of 2-amino-4H-3,1-benzothiazine (0.60 mmol) in toluene (20 ml) and TEA (0.10 mmol) in an inert gas atmosphere. The reaction mixture is refluxed for 5 hours then cooled and the solvent evaporated. The residue obtained is taken up with CH$_2$Cl$_2$. The organic phase is washed with H$_2$O, dried over Na$_2$SO$_4$ and concentrated, and the residue purified by resuspension in ethyl ether, then filtered and dried. The product is obtained with a yield of 33%. Recrystallisation from AcOEt gives a yellow solid, m.p. 191-196° C. $^1$H-NMR (DMSO-d$_6$): 1.19 (br s, 3H), 3.54 (br s, 2H), 4.02 (br s, 2H), 7.02-7.7.21 (m, 4H), 10.75 (br s, 1H), 11.91 (br s, 1H). MS (ESI): m/z 274 (M+Na$^+$).

1-(4H-3,1-benzothiazin-2-yl)-3-propylthiourea

Example 30

Prepared with a yield of 40%, similar to example 29 using n-propylisothiocyanate in place of ethylisothiocyanate. Recrystallisation from AcOEt gives a yellow solid with m.p. 180-184° C. $^1$H-NMR (DMSO-d$_6$): 0.95 (m, 3H), 1.64 (m, 2H), 3.53 (m, 2H), 4.02 (s, 2H), 7.05-7.27 (m, 4H), 10.78 (s, 1H), 11.99 (br s, 1H) MS (ESI): m/z 266 (M+H$^+$).

1-Ethyl-3-[6-(trifluoromethoxy)-4H-3,1-benzothiazin-2-yl]thiourea

Example 31

Prepared with a yield of 54%, similar to example 29 starting from 2-amino-6-trifluoromethoxy-4H-3,1-benzothiazine. The product is purified by chromatography through silica, eluting with CH$_2$Cl$_2$/petroleum ether (8:2), and recrystallisation from ACOEt gives a solid with m.p. 169-172° C. $^1$H-NMR (CDCl$_3$): 1.34 (t, J=7.2, 3H), 3.72 (m, 2H), 3.96 (s, 2H), 7.01-7.18 (m, 3H), 7.99 (br s, 1H), 11.53 (br s, 1H). MS (ESI): m/z 336 (M+H$^+$).

1-Propyl-3-[6-(trifluoromethoxy)-4H-3,1-benzothiazin-2-yl]thiourea

Example 32

Prepared with a yield of 47%, similar to example 29 starting from 2-amino-6-trifluoromethoxy-4H-3,1-benzothiazine and propylisothiocyanate. The product is purified by chromatography through silica, eluting with CH$_2$Cl$_2$/petroleum ether (8:2), and recrystallisation from n-hexane gives a white solid with m.p. 148-151° C. $^1$H-NMR (CDCl$_3$): 1.06 (t, J=7.4, 3H), 1.76 (m, 2H), 3.67 (q, J=6.3, 2H), 3.96 (s, 2H), 7.01-7.18 (m, 3H), 7.99 (s., 1H), 11.57 (br s, 1H). MS (ESI): m/z 350 (M+H$^+$).

1-Ethyl-3-[7-(trifluoromethoxy)-2H-1,4-benzothi-azin-3-yl]thiourea

Example 33

Similar to example 29, prepared with a yield of 67%, starting from 3-amino-7-trifluoromethoxy-2H-1,4-benzothiazine. The product is purified by chromatography through silica, eluting with $CH_2Cl_2$, and recrystallisation from AcOEt gives a white solid with m.p. 199-201° C. $^1$H-NMR (CDCl$_3$): 1.33 (t, J=7.3, 3H), 3.29 (s, 2H), 3.74 (m, 2H), 7.01-7.14 (m, 3H), 8.77 (br s, 1H), 11.93 (br s, 1H). MS (ESI): m/z 336 (M+H$^+$).

1-Propyl-3-(7-trifluoromethoxy-2H-1,4-benzothi-azin-3-yl)thiourea

Example 34

Similar to example 29, prepared with a yield of 71%, starting from 3-amino-7-trifluoromethoxy-2H-1,4-benzothiazine and propylisothiocyanate. The product is purified by chromatography through silica, eluting with $CH_2Cl_2$, and recrystallisation from n-hexane gives a white solid with m.p. 180-182° C. $^1$H-NMR (CDCl$_3$): 1.05 (t, J=7.4, 3H), 1.75 (m, 2H), 3.27 (s, 2H), 3.67 (q, J=6.3, 2H), 7.01-7.13 (m, 3H), 8.57 (br s, 1H), 11.97 (br s, 1H). MS (ESI): m/z 350 (M+H$^+$).

Evaluation of the Pharmacological Effects of the Compounds of the Invention

The neuroprotective activity of the products described in this invention have been assessed using an in vitro model of ischemia (oxygen-glucose deprivation/re-oxygenation, as detailed below), measuring the effect on glutamic acid release during re-oxygenation and the lactate dehydrogenase (LDH) activity released during said phase. Said in vitro ischemia model is generally accepted as a comprehensive model for the study and selection of products with neuroprotective activity.

Preparation of Cortical Slices

All experiments have been conducted in compliance with EEC regulations (86/609/CEE) regarding the use of laboratory animals.

Male Sprague-Dawley rats (350-450 g; Charles River Italia, Calco, Italy) have been sacrificed following anaesthesia (i.p. injection of 30 mg/kg ketamine hydrochloride and 8 mg/kg xylazine hydrochloride). The brain is rapidly removed and placed in aCSF (artificial Cerebro Spinal Fluid, composition expressed in mM: 120 NaCl, 2.5 KCl, 1.3 MgCl$_2$, 1.0 NaH$_2$PO$_4$, 1.5 CaCl$_2$, 26 NaHCO$_3$, 11 glucose, saturated with 95% O$_2$ −5% CO$_2$, with a final pH of 7.4, osmolarity 285-290 mOsmol). The cortex is removed and sectioned into slices 400 µm thick.

The slices are then maintained in oxygenated aCSF supplemented with 400 µM ascorbic acid for 1 hour at room temperature.

In Vitro Ischemia Conditions

Cortical slices total weight 33.6±2.6 mg, n=10) are incubated at 37° C., in 2 ml aCSF under a flow of 95% O$_2$/5% CO$_2$ for a period of 30 minutes. Oxygen-glucose deprivation is then implemented for 30 minutes by incubating in aCSF where the glucose has been substituted by sucrose and the oxygen mix air flow replaced with 95% N$_2$/5% CO$_2$. After the period of oxygen-glucose deprivation, the slices are placed in oxygenated aCSF for 90 minutes (re-oxygenation). In the treated samples, the compound of formula I is dissolved in aCSF at the concentrations described.

Evaluation of Neuronal Damage

Neuronal damage is assessed quantitatively by measuring the glutamate and lactate dehydrogenase (LDH) released into the aCSF during the period of re-oxygenation. In particular, glutamate is measured fluorimetrically (excitation at 366 nm; emission at 450 nm) using the conversion of NAD$^+$ to NADH catalysed by glutamate dehydrogenase (Eilers et al., 1999) while LDH activity is determined spectrophotometrically by measuring the reduction in absorbance at 340 nm via the oxidation of NADH to NAD$^+$ (Gay et al., 1968).

Data Analysis

All experiments have been conducted using slices obtained from at least 4 different rats. Data is reported as the S.E.M. and "n" is defined as the sample number. Data for glutamate and LDH activity is expressed as nmol/mg tissue and U/mg tissue, respectively. One unit (U) of LDH activity is defined as the correspondent yielding one micromole of lactate in one minute. Statistical analyses have been conducted using ANOVA followed by post-hoc Dunnett tests (GraphPad INSTAT v3.00, GraphPad Software, San Diego, Calif., USA).

Results:

The products of the invention have been remarkably effective in said model, in particular, the activity of said products is exemplified by the compounds reported below, with active results within the ranges indicated and dose-related responses within the 0.01-10 µM concentration range:

Example 5: N,N-dimethyl-N-[6-(trifluoromethoxy)benzothiazol-2-yl-]acetamidine, at concentrations of 0.1-1 µM, remarkable reduction in glutamate release.

Example 9: 1-Ethyl-3-[6-(trifluoromethoxy)benzothiazol-2-yl]thiourea, at concentrations of 0.1-1 µM, remarkable reduction in LDH activity.

Example 12: 1-Butyl-3-[6-(trifluoromethoxy)benzothiazol-2-yl]thiourea, at concentrations of 0.1-1 remarkable reduction in glutamate release.

Example 16: 1-Propyl-3-[6-(trifluoromethoxy)benzothiazol-2-yl]guanidine, at concentrations of 0.1-10 µM, remarkable reduction in glutamate release.

Example 17: N'-(4H-3,1-benzothiazin-2-yl)-N-methylacetamidine, at concentrations of 0.1-1 µM, remarkable reduction in glutamate release.

Example 18: N'-(4H-3,1-benzothiazin-2-yl)-N,N-dimethylacetamidine, at concentrations of 0.1-1 µM, remarkable reduction in glutamate release.

Example 19: N'-(4H-3,1-benzothiazin-2-yl)-N,N-diethylacetamidine, at concentrations of 0.1-1 remarkable reduction in glutamate release.

Example 21: N'-(2H-1,4-benzothiazin-3-yl)-N-methylacetamidine, at concentrations of 0.1-1 µM, remarkable reduction in glutamate release.

Wherein, "remarkable reduction" is meant a reduction in glutamic acid release and/or LDH activity to a value comprised of between 10% and 50% of that of the control sample.

In the same experimental paradigm used for the evaluation of the compounds of formula (I), a known voltage-dependent sodium channel blocker, Riluzole, within the same concentration interval used for the compounds of formula (I), has shown a reduction in glutamate release and LDH activity to values comprised of between 40% and 70% of the control sample.

Pharmaceutical Formulation of the Compounds of the Invention

The compounds of formula (I) may be used as they are, or as the pharmaceutically acceptable salts or solvates thereof, for the preparation of speciality pharmaceuticals for oral or parenteral administration for the treatment of the neurodegenerative pathologies forming the subject of the present invention. For all the formulations discussed herein, the compound of formula (I) will be administered in the treatment of the pathologies indicated, in quantities preferably comprised of between approx. 0.1 and approx. 20 mg/kg, this being the optimal quantity, with the number of daily administrations determined by the nature and severity of the pathology treated.

The present invention also includes pharmaceutical preparations containing a pharmacologically active quantity of a compound of formula (I), of the corresponding pharmaceutically acceptable salt and/or solvate, in combination with appropriate dispersants, lubricants and/or solvents. The compounds of the invention may be prepared in various oral pharmaceutical forms, such as: capsules, tablets, pills, granules. Appropriate dispersants and lubricants for said formulations include, but are not limited to: magnesium carbonate, magnesium stearate, talc, lactose, methylcellulose, sodium carboxymethylcellulose. The techniques used for the preparation of said formulations include mixing of the active ingredient with the dispersants, granulation and tabletting or capsule filling.

Other oral formulations include: emulsions, syrups and aqueous solutions. Emulsions may be prepared using appropriate agents such as lecithin, propylene glycol or sorbitan monooleate. Syrups and solutions may be prepared by suspending or dissolving the active ingredient in water with the addition of appropriate colorants and/or sweeteners, with or without appropriate stabilisers.

The compounds of the invention may be formulated for parenteral administration in the form of ampoules or prefilled syringes. The active ingredient may be dissolved in an aqueous carrier or be in the form of an oily emulsion.

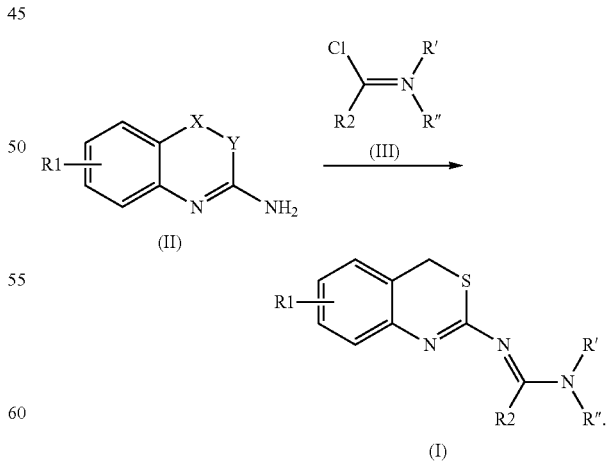

5. A process for the preparation of compounds of formula (I) wherein the Z group is a guanidine, as defined in claim 1, consisting of the reaction of a compound of formula (II) wherein the R$_1$, X and Y substituents have the same meanings reported in claim 1, with the cyanamide of formula R'R"N—CN, wherein the R' and R" substituents have the same meanings reported in claim 1:
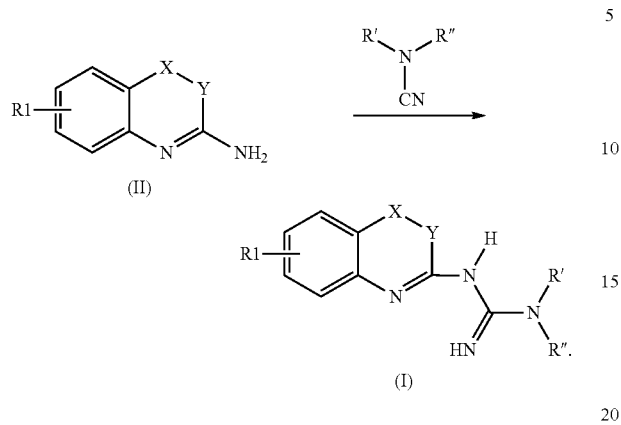

The invention claimed is:

1. A compound of Formula (I), a pharmaceutically acceptable salt, a tautomer and/or solvate thereof:

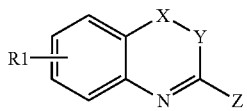

wherein:
X is a methylene group (—CH$_2$—)
Y is a sulphur atom (—S—)
Z is an amidine or guanidine group as reported below

Z:

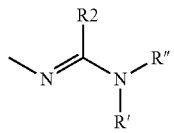 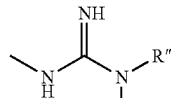

and where the R1, R2, R', R" substituents respectively are:
R1 is an atom of hydrogen (—H), fluorine (—F), chlorine (—Cl), a methoxy (—OCH$_3$), trifluoromethoxy (—OCF$_3$), trifluoromethyl (—CF$_3$) or methanesulphonyl (—SO$_2$CH$_3$) group; the R1 substituent being able to independently occupy the various positions available on the condensed phenyl; in a compound of formula (I) only one R1 substituent is present;
R2 is a C$_1$-C$_4$ alkyl group, an optionally substituted cyclopropyl (—C$_3$H$_5$), methylcyclopropyl (—CH$_2$C$_3$H$_5$), phenyl (-Ph) group or an optionally substituted benzyl (—CH$_2$Ph) group, where substituted phenyl or benzyl indicates the presence of no more than two substituents independently occupying the ortho, meta and para positions of the aromatic ring, independently selected from: fluorine (—F), chlorine (—Cl), methyl (—CH$_3$), methoxy (—OCH$_3$), hydroxyl (—OH), trifluoromethyl (—CF$_3$);
R' and R" are independently selected from: hydrogen (—H) and the groups defined above for R2;
provided that when X is a methylene group (—CH$_2$—) and Y is a sulphur atom (—S), in the compounds of formula (I) when R1 and R' are simultaneously a hydrogen atom (—H), R" is not one of the following groups: 4-methylphenyl, 3-chlorophenyl, or 4-chlorophenyl.

2. An oral pharmaceutical formulation including at least one of the compounds of formula (I) according to claim 1 as active ingredient, and at least one component selected from: carriers, binders, sweeteners and disaggregants commonly used in pharmaceutical formulations, or components that may aid absorption or allow controlled release of the drug as a function of time and/or gastrointestinal pH, as additional ingredients.

3. A parenteral (intravenous, intramuscular, subcutaneous) pharmaceutical formulation including at least one of the compounds of formula (I), according to claim 1, as active ingredient, and at least one component selected from aqueous carriers or oily emulsions, as additional ingredients.

4. A process for the preparation of compounds of formula (I) wherein the Z group is an amidine, as defined in claim 1, consisting of the reaction of a compound of formula (II) wherein the R$_1$, X and Y substituents have the same meanings reported in claim 1, with a chloroimine of formula (III), wherein the R$_2$, R' and R" substituents have the same meanings reported in claim 1: